US012799164B2

(12) United States Patent
Dodson et al.

(10) Patent No.: US 12,799,164 B2
(45) Date of Patent: Nov. 17, 2026

(54) AFFINITY AGENTS

(71) Applicant: Repligen Corporation, Waltham, MA (US)

(72) Inventors: William Scott Dodson, Lebanon, NH (US); Ethan Dow, Lebanon, NH (US); Yi Zhang, Lebanon, NH (US); Brandon Coyle, Oceanside, CA (US); Kelley Kearns, Grantham, NH (US); Warren Kett, West Lebanon, NH (US)

(73) Assignee: Repligen Corporation, Waltham, MA (US)

( * ) Notice: Subject to any disclaimer, the term of this patent is extended or adjusted under 35 U.S.C. 154(b) by 498 days.

(21) Appl. No.: 18/281,147

(22) PCT Filed: Mar. 10, 2022

(86) PCT No.: PCT/US2022/019839

§ 371 (c)(1),
(2) Date: Sep. 8, 2023

(87) PCT Pub. No.: WO2022/192597

PCT Pub. Date: Sep. 15, 2022

(65) Prior Publication Data

US 2024/0174717 A1 May 30, 2024

Related U.S. Application Data

(60) Provisional application No. 63/159,336, filed on Mar. 10, 2021.

(51) Int. Cl.
*C07K 7/56* (2006.01)
*B01J 20/32* (2006.01)

(52) U.S. Cl.
CPC ............ *C07K 7/56* (2013.01); *B01J 20/3219* (2013.01); *B01J 20/3274* (2013.01)

(58) Field of Classification Search
CPC ..... A61P 35/00; C12N 15/1037; A61K 38/00; C07K 2319/70
See application file for complete search history.

(56) References Cited

FOREIGN PATENT DOCUMENTS

| | | | |
|---|---|---|---|
| CN | 114207438 | A | 3/2022 |
| WO | 2014197840 | A1 | 12/2014 |
| WO | 2020242988 | A2 | 12/2020 |
| WO | 2021030777 | A1 | 2/2021 |

OTHER PUBLICATIONS

The International Search Report and Written Opinion mailed Sep. 6, 2022 for corresponding PCT/US22/19839 (12 pages).
Burkova et al., "Research Communication Exosomes from Human Placenta Purified by Affinity Chromatography on Sepharose Bearing Immobilized Antibodies Against CD81 Tetraspanin Contain Many Peptides and Small Proteins", IUBMB Life. Nov. 2018;70(11):1144-1155. doi: 10.1002/iub.1928. Epub Oct. 2, 2018. PMID: 30277306.
Marleau A.M, et al. "Exosome removal as a therapeutic adjuvant in cancer," Journal of Translational Medicine. vol. 10, No. 134, Jun. 27, 2012; pp. 1-12., figure 3; p. 8, col. 1, paragraph 1; DOI: 10.1186/1479-5876-10-134.
Kowal Joanna et al., "Proteomic comparison defines novel markers to characterize heterogeneous populations of extracellular vesicle subtypes," CrossMark, E968-E977, PNAS, Published online Feb. 8, 2016, 10 pages.
Chen Jiaci et al., "Review on Strategies and Technologies for Exosome Isolation and Purification," frontiers in Bioengineering and Biotechnology, published: Jan. 5, 2022, Jan. 2022 | vol. 9 | Article 811971, 18 pages.
Feng Kaixiang et al., "The Role of Exosomes in Thyroid Cancer and Their Potential Clinical Application," frontiers in Oncology, published: Dec. 1, 2020, Dec. 2020, vol. 10, Article 596132, 12 pages.
Zaborowski Mikołaj P. et al., "Extracellular Vesicles: Composition, Biological Relevance, and Methodsof Study," Overview Articles, Aug. 2015 / vol. 65 No. 8, BioScience 783, 15 pages.
Jyoti Madhusoodanan, "Care packages-Vesicles released in response to cigarette smokemight trigger COPD, but engineered versions offerpossible therapy," 2020 Springer Nature Limited, S10, Nature, vol. 581, May 14, 2020.

*Primary Examiner* — Melissa L Fisher
*Assistant Examiner* — Jia-Hai Lee
(74) *Attorney, Agent, or Firm* — KDW Firm PLLC

(57) ABSTRACT

Provided herein are affinity agents comprising ligands that specifically bind target molecules. The affinity agents are useful for binding, isolation, and/or purifications.

20 Claims, 6 Drawing Sheets

Specification includes a Sequence Listing.

SEQUENCE LISTING

```
<160> NUMBER OF SEQ ID NOS: 128

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: H or N
<220> FEATURE:
<221> NAME/KEY: MOD_RES
<222> LOCATION: (5)..(5)
<223> OTHER INFORMATION: Any amino acid
<220> FEATURE:
<221> NAME/KEY: SITE
<222> LOCATION: (5)..(14)
<223> OTHER INFORMATION: Cyclic
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (16)..(17)
<223> OTHER INFORMATION: S or T

<400> SEQUENCE: 1

Xaa Tyr Trp Arg Xaa Val Trp Phe Pro His Ala Gln Gly Xaa Val Xaa
1               5                   10                  15

Xaa
```

```
<210> SEQ ID NO 2
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

His Tyr Trp Arg Cys Val Trp Phe Pro His Ala Gln Gly Cys Val Ser
1               5                   10                  15

Thr Ala


<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asn Tyr Trp Arg Cys Val Trp Phe Pro His Ala Gln Gly Cys Val Ser
1               5                   10                  15

Thr Ala


<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Succinate

<400> SEQUENCE: 4

Tyr Trp Arg Cys Val Trp Phe Pro His Ala Gln Gly Cys Val Ser Thr
1               5                   10                  15

Ala


<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Trp Arg Cys Val Trp Phe Pro His Ala Gln Gly Cys Val Ser Thr
1               5                   10                  15

Ala


<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 3-(4-hydroxyphenyl)propionate

<400> SEQUENCE: 6
```

Trp Arg Cys Val Trp Phe Pro His Ala Gln Gly Cys Val Ser Thr Ala
1 5 10 15

<210> SEQ ID NO 7
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Acetyl
<220> FEATURE:
<223> OTHER INFORMATION: C-term Amide

<400> SEQUENCE: 7

His Tyr Trp Arg Cys Val Trp Phe Pro His Ala Gln Gly Cys Val Ser
1 5 10 15

Thr Ala

<210> SEQ ID NO 8
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Acetyl
<220> FEATURE:
<223> OTHER INFORMATION: C-term Amide

<400> SEQUENCE: 8

Asn Tyr Trp Arg Cys Val Trp Phe Pro His Ala Gln Gly Cys Val Ser
1 5 10 15

Thr Ala

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Succinate
<220> FEATURE:
<223> OTHER INFORMATION: C-term Amide

<400> SEQUENCE: 9

Tyr Trp Arg Cys Val Trp Phe Pro His Ala Gln Gly Cys Val Ser Thr
1 5 10 15

Ala

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Acetyl
<220> FEATURE:
<223> OTHER INFORMATION: C-term Amide

<400> SEQUENCE: 10

-continued

Tyr Trp Arg Cys Val Trp Phe Pro His Ala Gln Gly Cys Val Ser Thr
1               5                   10                  15

Ala

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: N-term 3-(4-hydroxyphenyl)propionate
<220> FEATURE:
<223> OTHER INFORMATION: C-term Amide

<400> SEQUENCE: 11

Trp Arg Cys Val Trp Phe Pro His Ala Gln Gly Cys Val Ser Thr Ala
1               5                   10                  15

<210> SEQ ID NO 12
<211> LENGTH: 19
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: N-term Acetyl
<220> FEATURE:
<221> NAME/KEY: MOD_RES
<222> LOCATION: (19)..(19)
<223> OTHER INFORMATION: (Peg)3Lys
<220> FEATURE:
<223> OTHER INFORMATION: C-term Amide

<400> SEQUENCE: 12

His Tyr Trp Arg Cys Val Trp Phe Pro His Ala Gln Gly Cys Val Ser
1               5                   10                  15

Thr Ala Lys

<210> SEQ ID NO 13
<211> LENGTH: 19
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: N-term Acetyl
<220> FEATURE:
<221> NAME/KEY: MOD_RES
<222> LOCATION: (19)..(19)
<223> OTHER INFORMATION: (Peg)3Lys
<220> FEATURE:
<223> OTHER INFORMATION: C-term Amide

<400> SEQUENCE: 13

Asn Tyr Trp Arg Cys Val Trp Phe Pro His Ala Gln Gly Cys Val Ser
1               5                   10                  15

Thr Ala Lys

<210> SEQ ID NO 14
<211> LENGTH: 18
<212> TYPE: PRT
<213> ORGANISM: Artificial Sequence
<220> FEATURE:
<223> OTHER INFORMATION: Description of Artificial Sequence: Synthetic
peptide <220> FEATURE:
<223> OTHER INFORMATION: N-term Succinate
<220> FEATURE:
<221> NAME/KEY: MOD_RES
<222> LOCATION: (18)..(18)
<223> OTHER INFORMATION: (Peg)3Lys
<220> FEATURE:
<223> OTHER INFORMATION: C-term Amide

<400> SEQUENCE: 14

Tyr Trp Arg Cys Val Trp Phe Pro His Ala Gln Gly Cys Val Ser Thr
1 5 10 15

Ala Lys

<210> SEQ ID NO 15
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Acetyl
<220> FEATURE:
<221> NAME/KEY: MOD_RES
<222> LOCATION: (18)..(18)
<223> OTHER INFORMATION: (Peg)3Lys
<220> FEATURE:
<223> OTHER INFORMATION: C-term Amide

<400> SEQUENCE: 15

Tyr Trp Arg Cys Val Trp Phe Pro His Ala Gln Gly Cys Val Ser Thr
1 5 10 15

Ala Lys

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term 3-(4-hydroxyphenyl)propionate
<220> FEATURE:
<221> NAME/KEY: MOD_RES
<222> LOCATION: (17)..(17)
<223> OTHER INFORMATION: (Peg)3Lys
<220> FEATURE:
<223> OTHER INFORMATION: C-term Amide

<400> SEQUENCE: 16

Trp Arg Cys Val Trp Phe Pro His Ala Gln Gly Cys Val Ser Thr Ala
1 5 10 15

Lys

<210> SEQ ID NO 17
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: SITE
<222> LOCATION: (5)..(14)
<223> OTHER INFORMATION: Cyclic

<400> SEQUENCE: 17

His Tyr Trp Arg Asp Val Trp Phe Pro His Ala Gln Gly Lys Val Ser
1 5 10 15

Thr Ala

<210> SEQ ID NO 18
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: SITE
<222> LOCATION: (5)..(14)
<223> OTHER INFORMATION: Cyclic

<400> SEQUENCE: 18

Asn Tyr Trp Arg Asp Val Trp Phe Pro His Ala Gln Gly Lys Val Ser
1 5 10 15

Thr Ala

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Succinate
<220> FEATURE:
<221> NAME/KEY: SITE
<222> LOCATION: (4)..(13)
<223> OTHER INFORMATION: Cyclic

<400> SEQUENCE: 19

Tyr Trp Arg Asp Val Trp Phe Pro His Ala Gln Gly Lys Val Ser Thr
1 5 10 15

Ala

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: SITE
<222> LOCATION: (4)..(13)
<223> OTHER INFORMATION: Cyclic

<400> SEQUENCE: 20

Tyr Trp Arg Asp Val Trp Phe Pro His Ala Gln Gly Lys Val Ser Thr
1 5 10 15

Ala

<210> SEQ ID NO 21
<211> LENGTH: 16
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term 3-(4-hydroxyphenyl)propionate
<220> FEATURE:
<221> NAME/KEY: SITE
<222> LOCATION: (3)..(12)
<223> OTHER INFORMATION: Cyclic

<400> SEQUENCE: 21

Trp Arg Asp Val Trp Phe Pro His Ala Gln Gly Lys Val Ser Thr Ala
1 5 10 15

<210> SEQ ID NO 22
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Acetyl
<220> FEATURE:
<221> NAME/KEY: SITE
<222> LOCATION: (5)..(14)
<223> OTHER INFORMATION: Cyclic
<220> FEATURE:
<223> OTHER INFORMATION: C-term Amide

<400> SEQUENCE: 22

His Tyr Trp Arg Asp Val Trp Phe Pro His Ala Gln Gly Lys Val Ser
1 5 10 15

Thr Ala

<210> SEQ ID NO 23
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Acetyl
<220> FEATURE:
<221> NAME/KEY: SITE
<222> LOCATION: (5)..(14)
<223> OTHER INFORMATION: Cyclic
<220> FEATURE:
<223> OTHER INFORMATION: C-term Amide

<400> SEQUENCE: 23

Asn Tyr Trp Arg Asp Val Trp Phe Pro His Ala Gln Gly Lys Val Ser
1 5 10 15

Thr Ala

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Succinate
<220> FEATURE:
<221> NAME/KEY: SITE
<222> LOCATION: (4)..(13)
<223> OTHER INFORMATION: Cyclic
<220> FEATURE:
<223> OTHER INFORMATION: C-term Amide

<400> SEQUENCE: 24

Tyr Trp Arg Asp Val Trp Phe Pro His Ala Gln Gly Lys Val Ser Thr
1 5 10 15

Ala

<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Acetyl
<220> FEATURE:
<221> NAME/KEY: SITE
<222> LOCATION: (4)..(13)
<223> OTHER INFORMATION: Cyclic
<220> FEATURE:
<223> OTHER INFORMATION: C-term Amide

<400> SEQUENCE: 25

```
Tyr Trp Arg Asp Val Trp Phe Pro His Ala Gln Gly Lys Val Ser Thr
1               5                   10                  15

Ala
```

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term 3-(4-hydroxyphenyl)propionate
<220> FEATURE:
<221> NAME/KEY: SITE
<222> LOCATION: (3)..(12)
<223> OTHER INFORMATION: Cyclic
<220> FEATURE:
<223> OTHER INFORMATION: C-term Amide

<400> SEQUENCE: 26

```
Trp Arg Asp Val Trp Phe Pro His Ala Gln Gly Lys Val Ser Thr Ala
1               5                   10                  15
```

<210> SEQ ID NO 27
<211> LENGTH: 19
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Acetyl
<220> FEATURE:
<221> NAME/KEY: SITE
<222> LOCATION: (5)..(14)
<223> OTHER INFORMATION: Cyclic
<220> FEATURE:
<221> NAME/KEY: MOD_RES
<222> LOCATION: (19)..(19)
<223> OTHER INFORMATION: (Peg)3Lys
<220> FEATURE:
<223> OTHER INFORMATION: C-term Amide

<400> SEQUENCE: 27

```
His Tyr Trp Arg Asp Val Trp Phe Pro His Ala Gln Gly Lys Val Ser
1               5                   10                  15

Thr Ala Lys
```

<210> SEQ ID NO 28
<211> LENGTH: 19
<212> TYPE: PRT

<213> ORGANISM: Artificial Sequence
<220> FEATURE:
<223> OTHER INFORMATION: Description of Artificial Sequence: Synthetic
peptide
<220> FEATURE:
<223> OTHER INFORMATION: N-term Acetyl
<220> FEATURE:
<221> NAME/KEY: SITE
<222> LOCATION: (5)..(14)
<223> OTHER INFORMATION: Cyclic
<220> FEATURE:
<221> NAME/KEY: MOD_RES
<222> LOCATION: (19)..(19)
<223> OTHER INFORMATION: (Peg)3Lys
<220> FEATURE:
<223> OTHER INFORMATION: C-term Amide

<400> SEQUENCE: 28

Asn Tyr Trp Arg Asp Val Trp Phe Pro His Ala Gln Gly Lys Val Ser
1 5 10 15

Thr Ala Lys

<210> SEQ ID NO 29
<211> LENGTH: 18
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: N-term Succinate
<220> FEATURE:
<221> NAME/KEY: SITE
<222> LOCATION: (4)..(13)
<223> OTHER INFORMATION: Cyclic
<220> FEATURE:
<221> NAME/KEY: MOD_RES
<222> LOCATION: (18)..(18)
<223> OTHER INFORMATION: (Peg)3Lys
<220> FEATURE:
<223> OTHER INFORMATION: C-term Amide

<400> SEQUENCE: 29

Tyr Trp Arg Asp Val Trp Phe Pro His Ala Gln Gly Lys Val Ser Thr
1 5 10 15

Ala Lys

<210> SEQ ID NO 30
<211> LENGTH: 18
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: N-term Acetyl
<220> FEATURE:
<221> NAME/KEY: SITE
<222> LOCATION: (4)..(13)
<223> OTHER INFORMATION: Cyclic
<220> FEATURE:
<221> NAME/KEY: MOD_RES
<222> LOCATION: (18)..(18)
<223> OTHER INFORMATION: (Peg)3Lys
<220> FEATURE:
<223> OTHER INFORMATION: C-term Amide

<400> SEQUENCE: 30

Tyr Trp Arg Asp Val Trp Phe Pro His Ala Gln Gly Lys Val Ser Thr
1 5 10 15

Ala Lys

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term 3-(4-hydroxyphenyl)propionate
<220> FEATURE:
<221> NAME/KEY: SITE
<222> LOCATION: (3)..(12)
<223> OTHER INFORMATION: Cyclic
<220> FEATURE:
<221> NAME/KEY: MOD_RES
<222> LOCATION: (17)..(17)
<223> OTHER INFORMATION: (Peg)3Lys
<220> FEATURE:
<223> OTHER INFORMATION: C-term Amide

<400> SEQUENCE: 31

```
Trp Arg Asp Val Trp Phe Pro His Ala Gln Gly Lys Val Ser Thr Ala
1               5                   10                  15

Lys
```

<210> SEQ ID NO 32
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: SITE
<222> LOCATION: (5)..(14)
<223> OTHER INFORMATION: Cyclic
<220> FEATURE:
<221> NAME/KEY: MOD_RES
<222> LOCATION: (14)..(14)
<223> OTHER INFORMATION: 2,3-diaminopropionic acid

<400> SEQUENCE: 32

```
His Tyr Trp Arg Asp Val Trp Phe Pro His Ala Gln Gly Xaa Val Ser
1               5                   10                  15

Thr Ala
```

<210> SEQ ID NO 33
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: SITE
<222> LOCATION: (5)..(14)
<223> OTHER INFORMATION: Cyclic
<220> FEATURE:
<221> NAME/KEY: MOD_RES
<222> LOCATION: (14)..(14)
<223> OTHER INFORMATION: 2,3-diaminopropionic acid

<400> SEQUENCE: 33

```
Asn Tyr Trp Arg Asp Val Trp Phe Pro His Ala Gln Gly Xaa Val Ser
1               5                   10                  15

Thr Ala
```

<210> SEQ ID NO 34

<211> LENGTH: 17
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: N-term Succinate
<220> FEATURE:
<221> NAME/KEY: SITE
<222> LOCATION: (4)..(13)
<223> OTHER INFORMATION: Cyclic
<220> FEATURE:
<221> NAME/KEY: MOD_RES
<222> LOCATION: (13)..(13)
<223> OTHER INFORMATION: 2,3-diaminopropionic acid

<400> SEQUENCE: 34

Tyr Trp Arg Asp Val Trp Phe Pro His Ala Gln Gly Xaa Val Ser Thr
1 5 10 15

Ala

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: SITE
<222> LOCATION: (4)..(13)
<223> OTHER INFORMATION: Cyclic
<220> FEATURE:
<221> NAME/KEY: MOD_RES
<222> LOCATION: (13)..(13)
<223> OTHER INFORMATION: 2,3-diaminopropionic acid

<400> SEQUENCE: 35

Tyr Trp Arg Asp Val Trp Phe Pro His Ala Gln Gly Xaa Val Ser Thr
1 5 10 15

Ala

<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: N-term 3-(4-hydroxyphenyl)propionate
<220> FEATURE:
<221> NAME/KEY: SITE
<222> LOCATION: (3)..(12)
<223> OTHER INFORMATION: Cyclic
<220> FEATURE:
<221> NAME/KEY: MOD_RES
<222> LOCATION: (12)..(12)
<223> OTHER INFORMATION: 2,3-diaminopropionic acid

<400> SEQUENCE: 36

Trp Arg Asp Val Trp Phe Pro His Ala Gln Gly Xaa Val Ser Thr Ala
1 5 10 15

<210> SEQ ID NO 37
<211> LENGTH: 18
<212> TYPE: PRT
<213> ORGANISM: Artificial Sequence
<220> FEATURE:
<223> OTHER INFORMATION: Description of Artificial Sequence: Synthetic

```
      peptide
<220> FEATURE:
<223> OTHER INFORMATION: N-term Acetyl
<220> FEATURE:
<221> NAME/KEY: SITE
<222> LOCATION: (5)..(14)
<223> OTHER INFORMATION: Cyclic
<220> FEATURE:
<221> NAME/KEY: MOD_RES
<222> LOCATION: (14)..(14)
<223> OTHER INFORMATION: 2,3-diaminopropionic acid
<220> FEATURE:
<223> OTHER INFORMATION: C-term Amide

<400> SEQUENCE: 37

His Tyr Trp Arg Asp Val Trp Phe Pro His Ala Gln Gly Xaa Val Ser
1               5                   10                  15

Thr Ala


<210> SEQ ID NO 38
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: SITE
<222> LOCATION: (5)..(14)
<223> OTHER INFORMATION: Cyclic
<220> FEATURE:
<221> NAME/KEY: MOD_RES
<222> LOCATION: (14)..(14)
<223> OTHER INFORMATION: 2,3-diaminopropionic acid
<220> FEATURE:
<223> OTHER INFORMATION: C-term Amide

<400> SEQUENCE: 38

Asn Tyr Trp Arg Asp Val Trp Phe Pro His Ala Gln Gly Xaa Val Ser
1               5                   10                  15

Thr Ala


<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Succinate
<220> FEATURE:
<221> NAME/KEY: SITE
<222> LOCATION: (4)..(13)
<223> OTHER INFORMATION: Cyclic
<220> FEATURE:
<221> NAME/KEY: MOD_RES
<222> LOCATION: (13)..(13)
<223> OTHER INFORMATION: 2,3-diaminopropionic acid
<220> FEATURE:
<223> OTHER INFORMATION: C-term Amide

<400> SEQUENCE: 39

Tyr Trp Arg Asp Val Trp Phe Pro His Ala Gln Gly Xaa Val Ser Thr
1               5                   10                  15

Ala


<210> SEQ ID NO 40
```

<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Acetyl
<220> FEATURE:
<221> NAME/KEY: SITE
<222> LOCATION: (4)..(13)
<223> OTHER INFORMATION: Cyclic
<220> FEATURE:
<221> NAME/KEY: MOD_RES
<222> LOCATION: (13)..(13)
<223> OTHER INFORMATION: 2,3-diaminopropionic acid
<220> FEATURE:
<223> OTHER INFORMATION: C-term Amide

<400> SEQUENCE: 40

```
Tyr Trp Arg Asp Val Trp Phe Pro His Ala Gln Gly Xaa Val Ser Thr
1               5                   10                  15

Ala
```

<210> SEQ ID NO 41
<211> LENGTH: 16
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term 3-(4-hydroxyphenyl)propionate
<220> FEATURE:
<221> NAME/KEY: SITE
<222> LOCATION: (3)..(12)
<223> OTHER INFORMATION: Cyclic
<220> FEATURE:
<221> NAME/KEY: MOD_RES
<222> LOCATION: (12)..(12)
<223> OTHER INFORMATION: 2,3-diaminopropionic acid
<220> FEATURE:
<223> OTHER INFORMATION: C-term Amide

<400> SEQUENCE: 41

```
Trp Arg Asp Val Trp Phe Pro His Ala Gln Gly Xaa Val Ser Thr Ala
1               5                   10                  15
```

<210> SEQ ID NO 42
<211> LENGTH: 19
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Acetyl
<220> FEATURE:
<221> NAME/KEY: SITE
<222> LOCATION: (5)..(14)
<223> OTHER INFORMATION: Cyclic
<220> FEATURE:
<221> NAME/KEY: MOD_RES
<222> LOCATION: (14)..(14)
<223> OTHER INFORMATION: 2,3-diaminopropionic acid
<220> FEATURE:
<221> NAME/KEY: MOD_RES
<222> LOCATION: (19)..(19)
<223> OTHER INFORMATION: (Peg)3Lys
<220> FEATURE:
<223> OTHER INFORMATION: C-term Amide

<400> SEQUENCE: 42

His Tyr Trp Arg Asp Val Trp Phe Pro His Ala Gln Gly Xaa Val Ser
1 5 10 15

Thr Ala Lys

<210> SEQ ID NO 43
<211> LENGTH: 19
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Acetyl
<220> FEATURE:
<221> NAME/KEY: SITE
<222> LOCATION: (5)..(14)
<223> OTHER INFORMATION: Cyclic
<220> FEATURE:
<221> NAME/KEY: MOD_RES
<222> LOCATION: (14)..(14)
<223> OTHER INFORMATION: 2,3-diaminopropionic acid
<220> FEATURE:
<221> NAME/KEY: MOD_RES
<222> LOCATION: (19)..(19)
<223> OTHER INFORMATION: (Peg)3Lys
<220> FEATURE:
<223> OTHER INFORMATION: C-term Amide

<400> SEQUENCE: 43

Asn Tyr Trp Arg Asp Val Trp Phe Pro His Ala Gln Gly Xaa Val Ser
1 5 10 15

Thr Ala Lys

<210> SEQ ID NO 44
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Succinate
<220> FEATURE:
<221> NAME/KEY: SITE
<222> LOCATION: (4)..(13)
<223> OTHER INFORMATION: Cyclic
<220> FEATURE:
<221> NAME/KEY: MOD_RES
<222> LOCATION: (13)..(13)
<223> OTHER INFORMATION: 2,3-diaminopropionic acid
<220> FEATURE:
<221> NAME/KEY: MOD_RES
<222> LOCATION: (18)..(18)
<223> OTHER INFORMATION: (Peg)3Lys
<220> FEATURE:
<223> OTHER INFORMATION: C-term Amide

<400> SEQUENCE: 44

Tyr Trp Arg Asp Val Trp Phe Pro His Ala Gln Gly Xaa Val Ser Thr
1 5 10 15

Ala Lys

<210> SEQ ID NO 45
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Acetyl
<220> FEATURE:
<221> NAME/KEY: SITE
<222> LOCATION: (4)..(13)
<223> OTHER INFORMATION: Cyclic
<220> FEATURE:
<221> NAME/KEY: MOD_RES
<222> LOCATION: (13)..(13)
<223> OTHER INFORMATION: 2,3-diaminopropionic acid
<220> FEATURE:
<221> NAME/KEY: MOD_RES
<222> LOCATION: (18)..(18)
<223> OTHER INFORMATION: (Peg)3Lys
<220> FEATURE:
<223> OTHER INFORMATION: C-term Amide

<400> SEQUENCE: 45

Tyr Trp Arg Asp Val Trp Phe Pro His Ala Gln Gly Xaa Val Ser Thr
1 5 10 15

Ala Lys

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term 3-(4-hydroxyphenyl)propionate
<220> FEATURE:
<221> NAME/KEY: SITE
<222> LOCATION: (3)..(12)
<223> OTHER INFORMATION: Cyclic
<220> FEATURE:
<221> NAME/KEY: MOD_RES
<222> LOCATION: (12)..(12)
<223> OTHER INFORMATION: 2,3-diaminopropionic acid
<220> FEATURE:
<221> NAME/KEY: MOD_RES
<222> LOCATION: (17)..(17)
<223> OTHER INFORMATION: (Peg)3Lys
<220> FEATURE:
<223> OTHER INFORMATION: C-term Amide

<400> SEQUENCE: 46

Trp Arg Asp Val Trp Phe Pro His Ala Gln Gly Xaa Val Ser Thr Ala
1 5 10 15

Lys

<210> SEQ ID NO 47
<211> LENGTH: 19
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Acetyl
<220> FEATURE:
<221> NAME/KEY: MOD_RES
<222> LOCATION: (19)..(19)
<223> OTHER INFORMATION: (Peg)3Lys(Biotin)
<220> FEATURE:
<223> OTHER INFORMATION: C-term Amide

<400> SEQUENCE: 47

His Tyr Trp Arg Cys Val Trp Phe Pro His Ala Gln Gly Cys Val Ser
1 5 10 15

Thr Ala Lys

```
<210> SEQ ID NO 48
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (19)..(19)
<223> OTHER INFORMATION: (Peg)3Lys(Biotin)
<220> FEATURE:
<223> OTHER INFORMATION: C-term Amide

<400> SEQUENCE: 48

Asn Tyr Trp Arg Cys Val Trp Phe Pro His Ala Gln Gly Cys Val Ser
1               5                   10                  15

Thr Ala Lys


<210> SEQ ID NO 49
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Succinate
<220> FEATURE:
<221> NAME/KEY: MOD_RES
<222> LOCATION: (18)..(18)
<223> OTHER INFORMATION: (Peg)3Lys(Biotin)
<220> FEATURE:
<223> OTHER INFORMATION: C-term Amide

<400> SEQUENCE: 49

Tyr Trp Arg Cys Val Trp Phe Pro His Ala Gln Gly Cys Val Ser Thr
1               5                   10                  15

Ala Lys


<210> SEQ ID NO 50
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (18)..(18)
<223> OTHER INFORMATION: (Peg)3Lys(Biotin)
<220> FEATURE:
<223> OTHER INFORMATION: C-term Amide

<400> SEQUENCE: 50

Tyr Trp Arg Cys Val Trp Phe Pro His Ala Gln Gly Cys Val Ser Thr
1               5                   10                  15

Ala Lys


<210> SEQ ID NO 51
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<220> FEATURE:
<223> OTHER INFORMATION: N-term 3-(4-hydroxyphenyl)propionate
<220> FEATURE:
<221> NAME/KEY: MOD_RES
<222> LOCATION: (17)..(17)
<223> OTHER INFORMATION: (Peg)3Lys(Biotin)
<220> FEATURE:
<223> OTHER INFORMATION: C-term Amide

<400> SEQUENCE: 51

Trp Arg Cys Val Trp Phe Pro His Ala Gln Gly Cys Val Ser Thr Ala
1 5 10 15

Lys

<210> SEQ ID NO 52
<211> LENGTH: 19
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: N-term Acetyl
<220> FEATURE:
<221> NAME/KEY: SITE
<222> LOCATION: (5)..(14)
<223> OTHER INFORMATION: Cyclic
<220> FEATURE:
<221> NAME/KEY: MOD_RES
<222> LOCATION: (19)..(19)
<223> OTHER INFORMATION: (Peg)3Lys(Biotin)
<220> FEATURE:
<223> OTHER INFORMATION: C-term Amide

<400> SEQUENCE: 52

His Tyr Trp Arg Asp Val Trp Phe Pro His Ala Gln Gly Lys Val Ser
1 5 10 15

Thr Ala Lys

<210> SEQ ID NO 53
<211> LENGTH: 19
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: N-term Acetyl
<220> FEATURE:
<221> NAME/KEY: SITE
<222> LOCATION: (5)..(14)
<223> OTHER INFORMATION: Cyclic
<220> FEATURE:
<221> NAME/KEY: MOD_RES
<222> LOCATION: (19)..(19)
<223> OTHER INFORMATION: (Peg)3Lys(Biotin)
<220> FEATURE:
<223> OTHER INFORMATION: C-term Amide

<400> SEQUENCE: 53

Asn Tyr Trp Arg Asp Val Trp Phe Pro His Ala Gln Gly Lys Val Ser
1 5 10 15

Thr Ala Lys

<210> SEQ ID NO 54
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Succinate
<220> FEATURE:
<221> NAME/KEY: SITE
<222> LOCATION: (4)..(13)
<223> OTHER INFORMATION: Cyclic
<220> FEATURE:
<221> NAME/KEY: MOD_RES
<222> LOCATION: (18)..(18)
<223> OTHER INFORMATION: (Peg)3Lys(Biotin)
<220> FEATURE:
<223> OTHER INFORMATION: C-term Amide

<400> SEQUENCE: 54

Tyr Trp Arg Asp Val Trp Phe Pro His Ala Gln Gly Lys Val Ser Thr
1 5 10 15

Ala Lys

<210> SEQ ID NO 55
<211> LENGTH: 18
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: N-term Acetyl
<220> FEATURE:
<221> NAME/KEY: SITE
<222> LOCATION: (4)..(13)
<223> OTHER INFORMATION: Cyclic
<220> FEATURE:
<221> NAME/KEY: MOD_RES
<222> LOCATION: (18)..(18)
<223> OTHER INFORMATION: (Peg)3Lys(Biotin)
<220> FEATURE:
<223> OTHER INFORMATION: C-term Amide

<400> SEQUENCE: 55

Tyr Trp Arg Asp Val Trp Phe Pro His Ala Gln Gly Lys Val Ser Thr
1 5 10 15

Ala Lys

<210> SEQ ID NO 56
<211> LENGTH: 17
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: N-term 3-(4-hydroxyphenyl)propionate
<220> FEATURE:
<221> NAME/KEY: SITE
<222> LOCATION: (3)..(12)
<223> OTHER INFORMATION: Cyclic
<220> FEATURE:
<221> NAME/KEY: MOD_RES
<222> LOCATION: (17)..(17)
<223> OTHER INFORMATION: (Peg)3Lys(Biotin)
<220> FEATURE:
<223> OTHER INFORMATION: C-term Amide

<400> SEQUENCE: 56

Trp Arg Asp Val Trp Phe Pro His Ala Gln Gly Lys Val Ser Thr Ala
1 5 10 15

Lys

<210> SEQ ID NO 57

```
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: SITE
<222> LOCATION: (5)..(14)
<223> OTHER INFORMATION: Cyclic
<220> FEATURE:
<221> NAME/KEY: MOD_RES
<222> LOCATION: (14)..(14)
<223> OTHER INFORMATION: 2,3-diaminopropionic acid
<220> FEATURE:
<221> NAME/KEY: MOD_RES
<222> LOCATION: (19)..(19)
<223> OTHER INFORMATION: (Peg)3Lys(Biotin)
<220> FEATURE:
<223> OTHER INFORMATION: C-term Amide

<400> SEQUENCE: 57

His Tyr Trp Arg Asp Val Trp Phe Pro His Ala Gln Gly Xaa Val Ser
1               5                   10                  15

Thr Ala Lys


<210> SEQ ID NO 58
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: SITE
<222> LOCATION: (5)..(14)
<223> OTHER INFORMATION: Cyclic
<220> FEATURE:
<221> NAME/KEY: MOD_RES
<222> LOCATION: (14)..(14)
<223> OTHER INFORMATION: 2,3-diaminopropionic acid
<220> FEATURE:
<221> NAME/KEY: MOD_RES
<222> LOCATION: (19)..(19)
<223> OTHER INFORMATION: (Peg)3Lys(Biotin)
<220> FEATURE:
<223> OTHER INFORMATION: C-term Amide

<400> SEQUENCE: 58

Asn Tyr Trp Arg Asp Val Trp Phe Pro His Ala Gln Gly Xaa Val Ser
1               5                   10                  15

Thr Ala Lys


<210> SEQ ID NO 59
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Succinate
<220> FEATURE:
<221> NAME/KEY: SITE
<222> LOCATION: (4)..(13)
<223> OTHER INFORMATION: Cyclic
<220> FEATURE:
<221> NAME/KEY: MOD_RES
<222> LOCATION: (13)..(13)
```

<223> OTHER INFORMATION: 2,3-diaminopropionic acid
<220> FEATURE:
<221> NAME/KEY: MOD_RES
<222> LOCATION: (18)..(18)
<223> OTHER INFORMATION: (Peg)3Lys(Biotin)
<220> FEATURE:
<223> OTHER INFORMATION: C-term Amide

<400> SEQUENCE: 59

Tyr Trp Arg Asp Val Trp Phe Pro His Ala Gln Gly Xaa Val Ser Thr
1 5 10 15

Ala Lys

<210> SEQ ID NO 60
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Acetyl
<220> FEATURE:
<221> NAME/KEY: SITE
<222> LOCATION: (4)..(13)
<223> OTHER INFORMATION: Cyclic
<220> FEATURE:
<221> NAME/KEY: MOD_RES
<222> LOCATION: (13)..(13)
<223> OTHER INFORMATION: 2,3-diaminopropionic acid
<220> FEATURE:
<221> NAME/KEY: MOD_RES
<222> LOCATION: (18)..(18)
<223> OTHER INFORMATION: (Peg)3Lys(Biotin)
<220> FEATURE:
<223> OTHER INFORMATION: C-term Amide

<400> SEQUENCE: 60

Tyr Trp Arg Asp Val Trp Phe Pro His Ala Gln Gly Xaa Val Ser Thr
1 5 10 15

Ala Lys

<210> SEQ ID NO 61
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term 3-(4-hydroxyphenyl)propionate
<220> FEATURE:
<221> NAME/KEY: SITE
<222> LOCATION: (3)..(12)
<223> OTHER INFORMATION: Cyclic
<220> FEATURE:
<221> NAME/KEY: MOD_RES
<222> LOCATION: (12)..(12)
<223> OTHER INFORMATION: 2,3-diaminopropionic acid
<220> FEATURE:
<221> NAME/KEY: MOD_RES
<222> LOCATION: (17)..(17)
<223> OTHER INFORMATION: (Peg)3Lys(Biotin)
<220> FEATURE:
<223> OTHER INFORMATION: C-term Amide

<400> SEQUENCE: 61

Trp Arg Asp Val Trp Phe Pro His Ala Gln Gly Xaa Val Ser Thr Ala
1 5 10 15

Lys

<210> SEQ ID NO 62
<211> LENGTH: 19
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: N-term Acetyl
<220> FEATURE:
<221> NAME/KEY: MOD_RES
<222> LOCATION: (19)..(19)
<223> OTHER INFORMATION: (Peg)3Lys(Biotin)
<220> FEATURE:
<223> OTHER INFORMATION: C-term Amide

<400> SEQUENCE: 62

His Tyr Trp Arg Cys Val Trp Phe Pro His Ala Gln Gly Cys Val Ala
1               5                   10                  15

Thr Ala Lys

<210> SEQ ID NO 63
<211> LENGTH: 19
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: N-term Acetyl
<220> FEATURE:
<221> NAME/KEY: MOD_RES
<222> LOCATION: (19)..(19)
<223> OTHER INFORMATION: (Peg)3Lys(Biotin)
<220> FEATURE:
<223> OTHER INFORMATION: C-term Amide

<400> SEQUENCE: 63

Asn Tyr Trp Arg Cys Val Trp Phe Pro His Ala Gln Gly Cys Val Ala
1               5                   10                  15

Thr Ala Lys

<210> SEQ ID NO 64
<211> LENGTH: 18
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: N-term Succinate
<220> FEATURE:
<221> NAME/KEY: MOD_RES
<222> LOCATION: (18)..(18)
<223> OTHER INFORMATION: (Peg)3Lys(Biotin)
<220> FEATURE:
<223> OTHER INFORMATION: C-term Amide

<400> SEQUENCE: 64

Tyr Trp Arg Cys Val Trp Phe Pro His Ala Gln Gly Cys Val Ala Thr
1               5                   10                  15

Ala Lys

<210> SEQ ID NO 65
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Acetyl
<220> FEATURE:
<221> NAME/KEY: MOD_RES
<222> LOCATION: (18)..(18)
<223> OTHER INFORMATION: (Peg)3Lys(Biotin)
<220> FEATURE:
<223> OTHER INFORMATION: C-term Amide

<400> SEQUENCE: 65

Tyr Trp Arg Cys Val Trp Phe Pro His Ala Gln Gly Cys Val Ala Thr
1 5 10 15

Ala Lys

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: N-term 3-(4-hydroxyphenyl)propionate
<220> FEATURE:
<221> NAME/KEY: MOD_RES
<222> LOCATION: (17)..(17)
<223> OTHER INFORMATION: (Peg)3Lys(Biotin)
<220> FEATURE:
<223> OTHER INFORMATION: C-term Amide

<400> SEQUENCE: 66

Trp Arg Cys Val Trp Phe Pro His Ala Gln Gly Cys Val Ala Thr Ala
1 5 10 15

Lys

<210> SEQ ID NO 67
<211> LENGTH: 19
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: N-term Acetyl
<220> FEATURE:
<221> NAME/KEY: SITE
<222> LOCATION: (5)..(14)
<223> OTHER INFORMATION: Cyclic
<220> FEATURE:
<221> NAME/KEY: MOD_RES
<222> LOCATION: (19)..(19)
<223> OTHER INFORMATION: (Peg)3Lys(Biotin)
<220> FEATURE:
<223> OTHER INFORMATION: C-term Amide

<400> SEQUENCE: 67

His Tyr Trp Arg Asp Val Trp Phe Pro His Ala Gln Gly Lys Val Ala
1 5 10 15

Thr Ala Lys

<210> SEQ ID NO 68
<211> LENGTH: 19
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: N-term Acetyl

```
<220> FEATURE:
<221> NAME/KEY: SITE
<222> LOCATION: (5)..(14)
<223> OTHER INFORMATION: Cyclic
<220> FEATURE:
<221> NAME/KEY: MOD_RES
<222> LOCATION: (19)..(19)
<223> OTHER INFORMATION: (Peg)3Lys(Biotin)
<220> FEATURE:
<223> OTHER INFORMATION: C-term Amide

<400> SEQUENCE: 68

Asn Tyr Trp Arg Asp Val Trp Phe Pro His Ala Gln Gly Lys Val Ala
1               5                   10                  15

Thr Ala Lys


<210> SEQ ID NO 69
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Succinate
<220> FEATURE:
<221> NAME/KEY: SITE
<222> LOCATION: (4)..(13)
<223> OTHER INFORMATION: Cyclic
<220> FEATURE:
<221> NAME/KEY: MOD_RES
<222> LOCATION: (18)..(18)
<223> OTHER INFORMATION: (Peg)3Lys(Biotin)
<220> FEATURE:
<223> OTHER INFORMATION: C-term Amide

<400> SEQUENCE: 69

Tyr Trp Arg Asp Val Trp Phe Pro His Ala Gln Gly Lys Val Ala Thr
1               5                   10                  15

Ala Lys


<210> SEQ ID NO 70
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: SITE
<222> LOCATION: (4)..(13)
<223> OTHER INFORMATION: Cyclic
<220> FEATURE:
<221> NAME/KEY: MOD_RES
<222> LOCATION: (18)..(18)
<223> OTHER INFORMATION: (Peg)3Lys(Biotin)
<220> FEATURE:
<223> OTHER INFORMATION: C-term Amide

<400> SEQUENCE: 70

Tyr Trp Arg Asp Val Trp Phe Pro His Ala Gln Gly Lys Val Ala Thr
1               5                   10                  15

Ala Lys


<210> SEQ ID NO 71
<211> LENGTH: 17
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: N-term 3-(4-hydroxyphenyl)propionate
<220> FEATURE:
<221> NAME/KEY: SITE
<222> LOCATION: (3)..(12)
<223> OTHER INFORMATION: Cyclic
<220> FEATURE:
<221> NAME/KEY: MOD_RES
<222> LOCATION: (17)..(17)
<223> OTHER INFORMATION: (Peg)3Lys(Biotin)
<220> FEATURE:
<223> OTHER INFORMATION: C-term Amide

<400> SEQUENCE: 71

Trp Arg Asp Val Trp Phe Pro His Ala Gln Gly Lys Val Ala Thr Ala
1               5                   10                  15

Lys


<210> SEQ ID NO 72
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: SITE
<222> LOCATION: (5)..(14)
<223> OTHER INFORMATION: Cyclic
<220> FEATURE:
<221> NAME/KEY: MOD_RES
<222> LOCATION: (14)..(14)
<223> OTHER INFORMATION: 2,3-diaminopropionic acid
<220> FEATURE:
<221> NAME/KEY: MOD_RES
<222> LOCATION: (19)..(19)
<223> OTHER INFORMATION: (Peg)3Lys(Biotin)
<220> FEATURE:
<223> OTHER INFORMATION: C-term Amide

<400> SEQUENCE: 72

His Tyr Trp Arg Asp Val Trp Phe Pro His Ala Gln Gly Xaa Val Ala
1               5                   10                  15

Thr Ala Lys


<210> SEQ ID NO 73
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: SITE
<222> LOCATION: (5)..(14)
<223> OTHER INFORMATION: Cyclic
<220> FEATURE:
<221> NAME/KEY: MOD_RES
<222> LOCATION: (14)..(14)
<223> OTHER INFORMATION: 2,3-diaminopropionic acid
<220> FEATURE:
<221> NAME/KEY: MOD_RES
<222> LOCATION: (19)..(19)
<223> OTHER INFORMATION: (Peg)3Lys(Biotin)
<220> FEATURE:
<223> OTHER INFORMATION: C-term Amide
```

<400> SEQUENCE: 73

Asn Tyr Trp Arg Asp Val Trp Phe Pro His Ala Gln Gly Xaa Val Ala
1 5 10 15

Thr Ala Lys

<210> SEQ ID NO 74
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Succinate
<220> FEATURE:
<221> NAME/KEY: SITE
<222> LOCATION: (4)..(13)
<223> OTHER INFORMATION: Cyclic
<220> FEATURE:
<221> NAME/KEY: MOD_RES
<222> LOCATION: (13)..(13)
<223> OTHER INFORMATION: 2,3-diaminopropionic acid
<220> FEATURE:
<221> NAME/KEY: MOD_RES
<222> LOCATION: (18)..(18)
<223> OTHER INFORMATION: (Peg)3Lys(Biotin)
<220> FEATURE:
<223> OTHER INFORMATION: C-term Amide

<400> SEQUENCE: 74

Tyr Trp Arg Asp Val Trp Phe Pro His Ala Gln Gly Xaa Val Ala Thr
1 5 10 15

Ala Lys

<210> SEQ ID NO 75
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Acetyl
<220> FEATURE:
<221> NAME/KEY: SITE
<222> LOCATION: (4)..(13)
<223> OTHER INFORMATION: Cyclic
<220> FEATURE:
<221> NAME/KEY: MOD_RES
<222> LOCATION: (13)..(13)
<223> OTHER INFORMATION: 2,3-diaminopropionic acid
<220> FEATURE:
<221> NAME/KEY: MOD_RES
<222> LOCATION: (18)..(18)
<223> OTHER INFORMATION: (Peg)3Lys(Biotin)
<220> FEATURE:
<223> OTHER INFORMATION: C-term Amide

<400> SEQUENCE: 75

Tyr Trp Arg Asp Val Trp Phe Pro His Ala Gln Gly Xaa Val Ala Thr
1 5 10 15

Ala Lys

<210> SEQ ID NO 76
<211> LENGTH: 17
<212> TYPE: PRT
<213> ORGANISM: Artificial Sequence
<220> FEATURE:
<223> OTHER INFORMATION: Description of Artificial Sequence: Synthetic

```
      peptide
<220> FEATURE:
<223> OTHER INFORMATION: N-term 3-(4-hydroxyphenyl)propionate
<220> FEATURE:
<221> NAME/KEY: SITE
<222> LOCATION: (3)..(12)
<223> OTHER INFORMATION: Cyclic
<220> FEATURE:
<221> NAME/KEY: MOD_RES
<222> LOCATION: (12)..(12)
<223> OTHER INFORMATION: 2,3-diaminopropionic acid
<220> FEATURE:
<221> NAME/KEY: MOD_RES
<222> LOCATION: (17)..(17)
<223> OTHER INFORMATION: (Peg)3Lys(Biotin)
<220> FEATURE:
<223> OTHER INFORMATION: C-term Amide

<400> SEQUENCE: 76

Trp Arg Asp Val Trp Phe Pro His Ala Gln Gly Xaa Val Ala Thr Ala
1               5                   10                  15

Lys


<210> SEQ ID NO 77
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (23)..(23)
<223> OTHER INFORMATION: Lys(Biotin)
<220> FEATURE:
<223> OTHER INFORMATION: C-term Amide

<400> SEQUENCE: 77

His Tyr Trp Arg Cys Val Trp Phe Pro His Ala Gln Gly Cys Val Ser
1               5                   10                  15

Thr Ala Pro Glu Gly Gly Lys
            20


<210> SEQ ID NO 78
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (23)..(23)
<223> OTHER INFORMATION: Lys(Biotin)
<220> FEATURE:
<223> OTHER INFORMATION: C-term Amide

<400> SEQUENCE: 78

Asn Tyr Trp Arg Cys Val Trp Phe Pro His Ala Gln Gly Cys Val Ser
1               5                   10                  15

Thr Ala Pro Glu Gly Gly Lys
            20


<210> SEQ ID NO 79
<211> LENGTH: 22
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Succinate
<220> FEATURE:
<221> NAME/KEY: MOD_RES
<222> LOCATION: (22)..(22)
<223> OTHER INFORMATION: Lys(Biotin)
<220> FEATURE:
<223> OTHER INFORMATION: C-term Amide

<400> SEQUENCE: 79

Tyr Trp Arg Cys Val Trp Phe Pro His Ala Gln Gly Cys Val Ser Thr
1               5                   10                  15

Ala Pro Glu Gly Gly Lys
            20


<210> SEQ ID NO 80
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (22)..(22)
<223> OTHER INFORMATION: Lys(Biotin)
<220> FEATURE:
<223> OTHER INFORMATION: C-term Amide

<400> SEQUENCE: 80

Tyr Trp Arg Cys Val Trp Phe Pro His Ala Gln Gly Cys Val Ser Thr
1               5                   10                  15

Ala Pro Glu Gly Gly Lys
            20


<210> SEQ ID NO 81
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 3-(4-hydroxyphenyl)propionate
<220> FEATURE:
<221> NAME/KEY: MOD_RES
<222> LOCATION: (21)..(21)
<223> OTHER INFORMATION: Lys(Biotin)
<220> FEATURE:
<223> OTHER INFORMATION: C-term Amide

<400> SEQUENCE: 81

Trp Arg Cys Val Trp Phe Pro His Ala Gln Gly Cys Val Ser Thr Ala
1               5                   10                  15

Pro Glu Gly Gly Lys
            20


<210> SEQ ID NO 82
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
```

<220> FEATURE:
<223> OTHER INFORMATION: N-term Acetyl
<220> FEATURE:
<221> NAME/KEY: SITE
<222> LOCATION: (5)..(14)
<223> OTHER INFORMATION: Cyclic
<220> FEATURE:
<221> NAME/KEY: MOD_RES
<222> LOCATION: (23)..(23)
<223> OTHER INFORMATION: Lys(Biotin)
<220> FEATURE:
<223> OTHER INFORMATION: C-term Amide

<400> SEQUENCE: 82

```
His Tyr Trp Arg Asp Val Trp Phe Pro His Ala Gln Gly Lys Val Ser
1               5                   10                  15

Thr Ala Pro Glu Gly Gly Lys
            20
```

<210> SEQ ID NO 83
<211> LENGTH: 23
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Acetyl
<220> FEATURE:
<221> NAME/KEY: SITE
<222> LOCATION: (5)..(14)
<223> OTHER INFORMATION: Cyclic
<220> FEATURE:
<221> NAME/KEY: MOD_RES
<222> LOCATION: (23)..(23)
<223> OTHER INFORMATION: Lys(Biotin)
<220> FEATURE:
<223> OTHER INFORMATION: C-term Amide

<400> SEQUENCE: 83

```
Asn Tyr Trp Arg Asp Val Trp Phe Pro His Ala Gln Gly Lys Val Ser
1               5                   10                  15

Thr Ala Pro Glu Gly Gly Lys
            20
```

<210> SEQ ID NO 84
<211> LENGTH: 22
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Succinate
<220> FEATURE:
<221> NAME/KEY: SITE
<222> LOCATION: (4)..(13)
<223> OTHER INFORMATION: Cyclic
<220> FEATURE:
<221> NAME/KEY: MOD_RES
<222> LOCATION: (22)..(22)
<223> OTHER INFORMATION: Lys(Biotin)
<220> FEATURE:
<223> OTHER INFORMATION: C-term Amide

<400> SEQUENCE: 84

```
Tyr Trp Arg Asp Val Trp Phe Pro His Ala Gln Gly Lys Val Ser Thr
1               5                   10                  15

Ala Pro Glu Gly Gly Lys
            20
```

```
<210> SEQ ID NO 85
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: SITE
<222> LOCATION: (4)..(13)
<223> OTHER INFORMATION: Cyclic
<220> FEATURE:
<221> NAME/KEY: MOD_RES
<222> LOCATION: (22)..(22)
<223> OTHER INFORMATION: Lys(Biotin)
<220> FEATURE:
<223> OTHER INFORMATION: C-term Amide

<400> SEQUENCE: 85

Tyr Trp Arg Asp Val Trp Phe Pro His Ala Gln Gly Lys Val Ser Thr
1               5                   10                  15

Ala Pro Glu Gly Gly Lys
            20


<210> SEQ ID NO 86
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 3-(4-hydroxyphenyl)propionate
<220> FEATURE:
<221> NAME/KEY: SITE
<222> LOCATION: (3)..(12)
<223> OTHER INFORMATION: Cyclic
<220> FEATURE:
<221> NAME/KEY: MOD_RES
<222> LOCATION: (21)..(21)
<223> OTHER INFORMATION: Lys(Biotin)
<220> FEATURE:
<223> OTHER INFORMATION: C-term Amide

<400> SEQUENCE: 86

Trp Arg Asp Val Trp Phe Pro His Ala Gln Gly Lys Val Ser Thr Ala
1               5                   10                  15

Pro Glu Gly Gly Lys
            20


<210> SEQ ID NO 87
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: SITE
<222> LOCATION: (5)..(14)
<223> OTHER INFORMATION: Cyclic
<220> FEATURE:
<221> NAME/KEY: MOD_RES
<222> LOCATION: (14)..(14)
<223> OTHER INFORMATION: 2,3-diaminopropionic acid
<220> FEATURE:
<221> NAME/KEY: MOD_RES
<222> LOCATION: (23)..(23)
```

<223> OTHER INFORMATION: Lys(Biotin)
<220> FEATURE:
<223> OTHER INFORMATION: C-term Amide

<400> SEQUENCE: 87

His Tyr Trp Arg Asp Val Trp Phe Pro His Ala Gln Gly Xaa Val Ser
1 5 10 15

Thr Ala Pro Glu Gly Gly Lys
20

<210> SEQ ID NO 88
<211> LENGTH: 23
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Acetyl
<220> FEATURE:
<221> NAME/KEY: SITE
<222> LOCATION: (5)..(14)
<223> OTHER INFORMATION: Cyclic
<220> FEATURE:
<221> NAME/KEY: MOD_RES
<222> LOCATION: (14)..(14)
<223> OTHER INFORMATION: 2,3-diaminopropionic acid
<220> FEATURE:
<221> NAME/KEY: MOD_RES
<222> LOCATION: (23)..(23)
<223> OTHER INFORMATION: Lys(Biotin)
<220> FEATURE:
<223> OTHER INFORMATION: C-term Amide

<400> SEQUENCE: 88

Asn Tyr Trp Arg Asp Val Trp Phe Pro His Ala Gln Gly Xaa Val Ser
1 5 10 15

Thr Ala Pro Glu Gly Gly Lys
20

<210> SEQ ID NO 89
<211> LENGTH: 22
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Succinate
<220> FEATURE:
<221> NAME/KEY: SITE
<222> LOCATION: (4)..(13)
<223> OTHER INFORMATION: Cyclic
<220> FEATURE:
<221> NAME/KEY: MOD_RES
<222> LOCATION: (13)..(13)
<223> OTHER INFORMATION: 2,3-diaminopropionic acid
<220> FEATURE:
<221> NAME/KEY: MOD_RES
<222> LOCATION: (22)..(22)
<223> OTHER INFORMATION: Lys(Biotin)
<220> FEATURE:
<223> OTHER INFORMATION: C-term Amide

<400> SEQUENCE: 89

Tyr Trp Arg Asp Val Trp Phe Pro His Ala Gln Gly Xaa Val Ser Thr
1 5 10 15

Ala Pro Glu Gly Gly Lys
20

```
<210> SEQ ID NO 90
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: SITE
<222> LOCATION: (4)..(13)
<223> OTHER INFORMATION: Cyclic
<220> FEATURE:
<221> NAME/KEY: MOD_RES
<222> LOCATION: (13)..(13)
<223> OTHER INFORMATION: 2,3-diaminopropionic acid
<220> FEATURE:
<221> NAME/KEY: MOD_RES
<222> LOCATION: (22)..(22)
<223> OTHER INFORMATION: Lys(Biotin)
<220> FEATURE:
<223> OTHER INFORMATION: C-term Amide

<400> SEQUENCE: 90

Tyr Trp Arg Asp Val Trp Phe Pro His Ala Gln Gly Xaa Val Ser Thr
1               5                   10                  15

Ala Pro Glu Gly Gly Lys
            20


<210> SEQ ID NO 91
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 3-(4-hydroxyphenyl)propionate
<220> FEATURE:
<221> NAME/KEY: SITE
<222> LOCATION: (3)..(12)
<223> OTHER INFORMATION: Cyclic
<220> FEATURE:
<221> NAME/KEY: MOD_RES
<222> LOCATION: (12)..(12)
<223> OTHER INFORMATION: 2,3-diaminopropionic acid
<220> FEATURE:
<221> NAME/KEY: MOD_RES
<222> LOCATION: (21)..(21)
<223> OTHER INFORMATION: Lys(Biotin)
<220> FEATURE:
<223> OTHER INFORMATION: C-term Amide

<400> SEQUENCE: 91

Trp Arg Asp Val Trp Phe Pro His Ala Gln Gly Xaa Val Ser Thr Ala
1               5                   10                  15

Pro Glu Gly Gly Lys
            20


<210> SEQ ID NO 92
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (23)..(23)
<223> OTHER INFORMATION: Lys(Biotin)
```

<220> FEATURE:
<223> OTHER INFORMATION: C-term Amide

<400> SEQUENCE: 92

His Tyr Trp Arg Cys Val Trp Phe Pro His Ala Gln Gly Cys Val Ala
1 5 10 15

Thr Ala Pro Glu Gly Gly Lys
20

<210> SEQ ID NO 93
<211> LENGTH: 23
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Acetyl
<220> FEATURE:
<221> NAME/KEY: MOD_RES
<222> LOCATION: (23)..(23)
<223> OTHER INFORMATION: Lys(Biotin)
<220> FEATURE:
<223> OTHER INFORMATION: C-term Amide

<400> SEQUENCE: 93

Asn Tyr Trp Arg Cys Val Trp Phe Pro His Ala Gln Gly Cys Val Ala
1 5 10 15

Thr Ala Pro Glu Gly Gly Lys
20

<210> SEQ ID NO 94
<211> LENGTH: 22
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Succinate
<220> FEATURE:
<221> NAME/KEY: MOD_RES
<222> LOCATION: (22)..(22)
<223> OTHER INFORMATION: Lys(Biotin)
<220> FEATURE:
<223> OTHER INFORMATION: C-term Amide

<400> SEQUENCE: 94

Tyr Trp Arg Cys Val Trp Phe Pro His Ala Gln Gly Cys Val Ala Thr
1 5 10 15

Ala Pro Glu Gly Gly Lys
20

<210> SEQ ID NO 95
<211> LENGTH: 22
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Acetyl
<220> FEATURE:
<221> NAME/KEY: MOD_RES
<222> LOCATION: (22)..(22)
<223> OTHER INFORMATION: Lys(Biotin)
<220> FEATURE:
<223> OTHER INFORMATION: C-term Amide

<400> SEQUENCE: 95

```
Tyr Trp Arg Cys Val Trp Phe Pro His Ala Gln Gly Cys Val Ala Thr
1               5                   10                  15

Ala Pro Glu Gly Gly Lys
            20


<210> SEQ ID NO 96
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 3-(4-hydroxyphenyl)propionate
<220> FEATURE:
<221> NAME/KEY: MOD_RES
<222> LOCATION: (21)..(21)
<223> OTHER INFORMATION: Lys(Biotin)
<220> FEATURE:
<223> OTHER INFORMATION: C-term Amide

<400> SEQUENCE: 96

Trp Arg Cys Val Trp Phe Pro His Ala Gln Gly Cys Val Ala Thr Ala
1               5                   10                  15

Pro Glu Gly Gly Lys
            20


<210> SEQ ID NO 97
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: SITE
<222> LOCATION: (5)..(14)
<223> OTHER INFORMATION: Cyclic
<220> FEATURE:
<221> NAME/KEY: MOD_RES
<222> LOCATION: (23)..(23)
<223> OTHER INFORMATION: Lys(Biotin)
<220> FEATURE:
<223> OTHER INFORMATION: C-term Amide

<400> SEQUENCE: 97

His Tyr Trp Arg Asp Val Trp Phe Pro His Ala Gln Gly Lys Val Ala
1               5                   10                  15

Thr Ala Pro Glu Gly Gly Lys
            20


<210> SEQ ID NO 98
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: SITE
<222> LOCATION: (5)..(14)
<223> OTHER INFORMATION: Cyclic
<220> FEATURE:
<221> NAME/KEY: MOD_RES
<222> LOCATION: (23)..(23)
<223> OTHER INFORMATION: Lys(Biotin)
```

```
<220> FEATURE:
<223> OTHER INFORMATION: C-term Amide

<400> SEQUENCE: 98

Asn Tyr Trp Arg Asp Val Trp Phe Pro His Ala Gln Gly Lys Val Ala
1               5                   10                  15

Thr Ala Pro Glu Gly Gly Lys
            20


<210> SEQ ID NO 99
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Succinate
<220> FEATURE:
<221> NAME/KEY: SITE
<222> LOCATION: (4)..(13)
<223> OTHER INFORMATION: Cyclic
<220> FEATURE:
<221> NAME/KEY: MOD_RES
<222> LOCATION: (22)..(22)
<223> OTHER INFORMATION: Lys(Biotin)
<220> FEATURE:
<223> OTHER INFORMATION: C-term Amide

<400> SEQUENCE: 99

Tyr Trp Arg Asp Val Trp Phe Pro His Ala Gln Gly Lys Val Ala Thr
1               5                   10                  15

Ala Pro Glu Gly Gly Lys
            20


<210> SEQ ID NO 100
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: SITE
<222> LOCATION: (4)..(13)
<223> OTHER INFORMATION: Cyclic
<220> FEATURE:
<221> NAME/KEY: MOD_RES
<222> LOCATION: (22)..(22)
<223> OTHER INFORMATION: Lys(Biotin)
<220> FEATURE:
<223> OTHER INFORMATION: C-term Amide

<400> SEQUENCE: 100

Tyr Trp Arg Asp Val Trp Phe Pro His Ala Gln Gly Lys Val Ala Thr
1               5                   10                  15

Ala Pro Glu Gly Gly Lys
            20


<210> SEQ ID NO 101
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 3-(4-hydroxyphenyl)propionate
```

```
<220> FEATURE:
<221> NAME/KEY: SITE
<222> LOCATION: (3)..(12)
<223> OTHER INFORMATION: Cyclic
<220> FEATURE:
<221> NAME/KEY: MOD_RES
<222> LOCATION: (21)..(21)
<223> OTHER INFORMATION: Lys(Biotin)
<220> FEATURE:
<223> OTHER INFORMATION: C-term Amide

<400> SEQUENCE: 101

Trp Arg Asp Val Trp Phe Pro His Ala Gln Gly Lys Val Ala Thr Ala
1               5                   10                  15

Pro Glu Gly Gly Lys
            20


<210> SEQ ID NO 102
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: SITE
<222> LOCATION: (5)..(14)
<223> OTHER INFORMATION: Cyclic
<220> FEATURE:
<221> NAME/KEY: MOD_RES
<222> LOCATION: (14)..(14)
<223> OTHER INFORMATION: 2,3-diaminopropionic acid
<220> FEATURE:
<221> NAME/KEY: MOD_RES
<222> LOCATION: (23)..(23)
<223> OTHER INFORMATION: Lys(Biotin)
<220> FEATURE:
<223> OTHER INFORMATION: C-term Amide

<400> SEQUENCE: 102

His Tyr Trp Arg Asp Val Trp Phe Pro His Ala Gln Gly Xaa Val Ala
1               5                   10                  15

Thr Ala Pro Glu Gly Gly Lys
            20


<210> SEQ ID NO 103
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: SITE
<222> LOCATION: (5)..(14)
<223> OTHER INFORMATION: Cyclic
<220> FEATURE:
<221> NAME/KEY: MOD_RES
<222> LOCATION: (14)..(14)
<223> OTHER INFORMATION: 2,3-diaminopropionic acid
<220> FEATURE:
<221> NAME/KEY: MOD_RES
<222> LOCATION: (23)..(23)
<223> OTHER INFORMATION: Lys(Biotin)
<220> FEATURE:
<223> OTHER INFORMATION: C-term Amide

<400> SEQUENCE: 103
```

```
Asn Tyr Trp Arg Asp Val Trp Phe Pro His Ala Gln Gly Xaa Val Ala
1               5                   10                  15

Thr Ala Pro Glu Gly Gly Lys
            20


<210> SEQ ID NO 104
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Succinate
<220> FEATURE:
<221> NAME/KEY: SITE
<222> LOCATION: (4)..(13)
<223> OTHER INFORMATION: Cyclic
<220> FEATURE:
<221> NAME/KEY: MOD_RES
<222> LOCATION: (13)..(13)
<223> OTHER INFORMATION: 2,3-diaminopropionic acid
<220> FEATURE:
<221> NAME/KEY: MOD_RES
<222> LOCATION: (22)..(22)
<223> OTHER INFORMATION: Lys(Biotin)
<220> FEATURE:
<223> OTHER INFORMATION: C-term Amide

<400> SEQUENCE: 104

Tyr Trp Arg Asp Val Trp Phe Pro His Ala Gln Gly Xaa Val Ala Thr
1               5                   10                  15

Ala Pro Glu Gly Gly Lys
            20


<210> SEQ ID NO 105
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: SITE
<222> LOCATION: (4)..(13)
<223> OTHER INFORMATION: Cyclic
<220> FEATURE:
<221> NAME/KEY: MOD_RES
<222> LOCATION: (13)..(13)
<223> OTHER INFORMATION: 2,3-diaminopropionic acid
<220> FEATURE:
<221> NAME/KEY: MOD_RES
<222> LOCATION: (22)..(22)
<223> OTHER INFORMATION: Lys(Biotin)
<220> FEATURE:
<223> OTHER INFORMATION: C-term Amide

<400> SEQUENCE: 105

Tyr Trp Arg Asp Val Trp Phe Pro His Ala Gln Gly Xaa Val Ala Thr
1               5                   10                  15

Ala Pro Glu Gly Gly Lys
            20


<210> SEQ ID NO 106
<211> LENGTH: 21
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<223> OTHER INFORMATION: N-term 3-(4-hydroxyphenyl)propionate
<220> FEATURE:
<221> NAME/KEY: SITE
<222> LOCATION: (3)..(12)
<223> OTHER INFORMATION: Cyclic
<220> FEATURE:
<221> NAME/KEY: MOD_RES
<222> LOCATION: (12)..(12)
<223> OTHER INFORMATION: 2,3-diaminopropionic acid
<220> FEATURE:
<221> NAME/KEY: MOD_RES
<222> LOCATION: (21)..(21)
<223> OTHER INFORMATION: Lys(Biotin)
<220> FEATURE:
<223> OTHER INFORMATION: C-term Amide

<400> SEQUENCE: 106

Trp Arg Asp Val Trp Phe Pro His Ala Gln Gly Xaa Val Ala Thr Ala
1               5                   10                  15

Pro Glu Gly Gly Lys
            20


<210> SEQ ID NO 107
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (5)..(14)
<223> OTHER INFORMATION: Cyclic
<220> FEATURE:
<221> NAME/KEY: MOD_RES
<222> LOCATION: (14)..(14)
<223> OTHER INFORMATION: 2,3-diaminopropionic acid

<400> SEQUENCE: 107

His Tyr Trp Arg Asp Val Trp Phe Pro His Ala Gln Gly Xaa Val Ala
1               5                   10                  15

Thr Ala


<210> SEQ ID NO 108
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (5)..(14)
<223> OTHER INFORMATION: Cyclic
<220> FEATURE:
<221> NAME/KEY: MOD_RES
<222> LOCATION: (14)..(14)
<223> OTHER INFORMATION: 2,3-diaminopropionic acid

<400> SEQUENCE: 108

Asn Tyr Trp Arg Asp Val Trp Phe Pro His Ala Gln Gly Xaa Val Ala
1               5                   10                  15

Thr Ala


<210> SEQ ID NO 109
<211> LENGTH: 17
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: N-term Succinate
<220> FEATURE:
<221> NAME/KEY: SITE
<222> LOCATION: (4)..(13)
<223> OTHER INFORMATION: Cyclic
<220> FEATURE:
<221> NAME/KEY: MOD_RES
<222> LOCATION: (13)..(13)
<223> OTHER INFORMATION: 2,3-diaminopropionic acid

<400> SEQUENCE: 109

Tyr Trp Arg Asp Val Trp Phe Pro His Ala Gln Gly Xaa Val Ala Thr
1               5                   10                  15

Ala


<210> SEQ ID NO 110
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (4)..(13)
<223> OTHER INFORMATION: Cyclic
<220> FEATURE:
<221> NAME/KEY: MOD_RES
<222> LOCATION: (13)..(13)
<223> OTHER INFORMATION: 2,3-diaminopropionic acid

<400> SEQUENCE: 110

Tyr Trp Arg Asp Val Trp Phe Pro His Ala Gln Gly Xaa Val Ala Thr
1               5                   10                  15

Ala


<210> SEQ ID NO 111
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 3-(4-hydroxyphenyl)propionate
<220> FEATURE:
<221> NAME/KEY: SITE
<222> LOCATION: (3)..(12)
<223> OTHER INFORMATION: Cyclic
<220> FEATURE:
<221> NAME/KEY: MOD_RES
<222> LOCATION: (12)..(12)
<223> OTHER INFORMATION: 2,3-diaminopropionic acid

<400> SEQUENCE: 111

Trp Arg Asp Val Trp Phe Pro His Ala Gln Gly Xaa Val Ala Thr Ala
1               5                   10                  15


<210> SEQ ID NO 112
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
```

<220> FEATURE:
<221> NAME/KEY: SITE
<222> LOCATION: (5)..(14)
<223> OTHER INFORMATION: Cyclic
<220> FEATURE:
<221> NAME/KEY: MOD_RES
<222> LOCATION: (14)..(14)
<223> OTHER INFORMATION: 2,3-diaminopropionic acid
<220> FEATURE:
<223> OTHER INFORMATION: C-term Amide

<400> SEQUENCE: 112

His Tyr Trp Arg Asp Val Trp Phe Pro His Ala Gln Gly Xaa Val Ala
1 5 10 15

Thr Ala

<210> SEQ ID NO 113
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Acetyl
<220> FEATURE:
<221> NAME/KEY: SITE
<222> LOCATION: (5)..(14)
<223> OTHER INFORMATION: Cyclic
<220> FEATURE:
<221> NAME/KEY: MOD_RES
<222> LOCATION: (14)..(14)
<223> OTHER INFORMATION: 2,3-diaminopropionic acid
<220> FEATURE:
<223> OTHER INFORMATION: C-term Amide

<400> SEQUENCE: 113

Asn Tyr Trp Arg Asp Val Trp Phe Pro His Ala Gln Gly Xaa Val Ala
1 5 10 15

Thr Ala

<210> SEQ ID NO 114
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Succinate
<220> FEATURE:
<221> NAME/KEY: SITE
<222> LOCATION: (4)..(13)
<223> OTHER INFORMATION: Cyclic
<220> FEATURE:
<221> NAME/KEY: MOD_RES
<222> LOCATION: (13)..(13)
<223> OTHER INFORMATION: 2,3-diaminopropionic acid
<220> FEATURE:
<223> OTHER INFORMATION: C-term Amide

<400> SEQUENCE: 114

Tyr Trp Arg Asp Val Trp Phe Pro His Ala Gln Gly Xaa Val Ala Thr
1 5 10 15

Ala

<210> SEQ ID NO 115
<211> LENGTH: 17
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: SITE
<222> LOCATION: (4)..(13)
<223> OTHER INFORMATION: Cyclic
<220> FEATURE:
<221> NAME/KEY: MOD_RES
<222> LOCATION: (13)..(13)
<223> OTHER INFORMATION: 2,3-diaminopropionic acid
<220> FEATURE:
<223> OTHER INFORMATION: C-term Amide

<400> SEQUENCE: 115

Tyr Trp Arg Asp Val Trp Phe Pro His Ala Gln Gly Xaa Val Ala Thr
1               5                   10                  15

Ala


<210> SEQ ID NO 116
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 3-(4-hydroxyphenyl)propionate
<220> FEATURE:
<221> NAME/KEY: SITE
<222> LOCATION: (3)..(12)
<223> OTHER INFORMATION: Cyclic
<220> FEATURE:
<221> NAME/KEY: MOD_RES
<222> LOCATION: (12)..(12)
<223> OTHER INFORMATION: 2,3-diaminopropionic acid
<220> FEATURE:
<223> OTHER INFORMATION: C-term Amide

<400> SEQUENCE: 116

Trp Arg Asp Val Trp Phe Pro His Ala Gln Gly Xaa Val Ala Thr Ala
1               5                   10                  15


<210> SEQ ID NO 117
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: SITE
<222> LOCATION: (5)..(14)
<223> OTHER INFORMATION: Cyclic
<220> FEATURE:
<221> NAME/KEY: MOD_RES
<222> LOCATION: (14)..(14)
<223> OTHER INFORMATION: 2,3-diaminopropionic acid
<220> FEATURE:
<221> NAME/KEY: MOD_RES
<222> LOCATION: (19)..(19)
<223> OTHER INFORMATION: (Peg)3Lys
<220> FEATURE:
<223> OTHER INFORMATION: C-term Amide

<400> SEQUENCE: 117

His Tyr Trp Arg Asp Val Trp Phe Pro His Ala Gln Gly Xaa Val Ala
1               5                   10                  15
```

Thr Ala Lys

<210> SEQ ID NO 118
<211> LENGTH: 19
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Acetyl
<220> FEATURE:
<221> NAME/KEY: SITE
<222> LOCATION: (5)..(14)
<223> OTHER INFORMATION: Cyclic
<220> FEATURE:
<221> NAME/KEY: MOD_RES
<222> LOCATION: (14)..(14)
<223> OTHER INFORMATION: 2,3-diaminopropionic acid
<220> FEATURE:
<221> NAME/KEY: MOD_RES
<222> LOCATION: (19)..(19)
<223> OTHER INFORMATION: (Peg)3Lys
<220> FEATURE:
<223> OTHER INFORMATION: C-term Amide

<400> SEQUENCE: 118

Asn Tyr Trp Arg Asp Val Trp Phe Pro His Ala Gln Gly Xaa Val Ala
1 5 10 15

Thr Ala Lys

<210> SEQ ID NO 119
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Succinate
<220> FEATURE:
<221> NAME/KEY: SITE
<222> LOCATION: (4)..(13)
<223> OTHER INFORMATION: Cyclic
<220> FEATURE:
<221> NAME/KEY: MOD_RES
<222> LOCATION: (13)..(13)
<223> OTHER INFORMATION: 2,3-diaminopropionic acid
<220> FEATURE:
<221> NAME/KEY: MOD_RES
<222> LOCATION: (18)..(18)
<223> OTHER INFORMATION: (Peg)3Lys
<220> FEATURE:
<223> OTHER INFORMATION: C-term Amide

<400> SEQUENCE: 119

Tyr Trp Arg Asp Val Trp Phe Pro His Ala Gln Gly Xaa Val Ala Thr
1 5 10 15

Ala Lys

<210> SEQ ID NO 120
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Acetyl
<220> FEATURE:
<221> NAME/KEY: SITE
<222> LOCATION: (4)..(13)

<223> OTHER INFORMATION: Cyclic
<220> FEATURE:
<221> NAME/KEY: MOD_RES
<222> LOCATION: (13)..(13)
<223> OTHER INFORMATION: 2,3-diaminopropionic acid
<220> FEATURE:
<221> NAME/KEY: MOD_RES
<222> LOCATION: (18)..(18)
<223> OTHER INFORMATION: (Peg)3Lys
<220> FEATURE:
<223> OTHER INFORMATION: C-term Amide

<400> SEQUENCE: 120

```
Tyr Trp Arg Asp Val Trp Phe Pro His Ala Gln Gly Xaa Val Ala Thr
1               5                   10                  15

Ala Lys
```

<210> SEQ ID NO 121
<211> LENGTH: 17
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term 3-(4-hydroxyphenyl)propionate
<220> FEATURE:
<221> NAME/KEY: SITE
<222> LOCATION: (3)..(12)
<223> OTHER INFORMATION: Cyclic
<220> FEATURE:
<221> NAME/KEY: MOD_RES
<222> LOCATION: (12)..(12)
<223> OTHER INFORMATION: 2,3-diaminopropionic acid
<220> FEATURE:
<221> NAME/KEY: MOD_RES
<222> LOCATION: (17)..(17)
<223> OTHER INFORMATION: (Peg)3Lys
<220> FEATURE:
<223> OTHER INFORMATION: C-term Amide

<400> SEQUENCE: 121

```
Trp Arg Asp Val Trp Phe Pro His Ala Gln Gly Xaa Val Ala Thr Ala
1               5                   10                  15

Lys
```

<210> SEQ ID NO 122
<211> LENGTH: 23
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term Acetyl
<220> FEATURE:
<221> NAME/KEY: SITE
<222> LOCATION: (5)..(14)
<223> OTHER INFORMATION: Cyclic
<220> FEATURE:
<221> NAME/KEY: MOD_RES
<222> LOCATION: (14)..(14)
<223> OTHER INFORMATION: 2,3-diaminopropionic acid
<220> FEATURE:
<223> OTHER INFORMATION: C-term Amide

<400> SEQUENCE: 122

```
His Tyr Trp Arg Asp Val Trp Phe Pro His Ala Gln Gly Xaa Val Ala
1               5                   10                  15

Thr Ala Pro Glu Gly Gly Lys
            20
```

<210> SEQ ID NO 123
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: SITE
<222> LOCATION: (5)..(14)
<223> OTHER INFORMATION: Cyclic
<220> FEATURE:
<221> NAME/KEY: MOD_RES
<222> LOCATION: (14)..(14)
<223> OTHER INFORMATION: 2,3-diaminopropionic acid
<220> FEATURE:
<223> OTHER INFORMATION: C-term Amide

<400> SEQUENCE: 123

```
Asn Tyr Trp Arg Asp Val Trp Phe Pro His Ala Gln Gly Xaa Val Ala
1               5                   10                  15

Thr Ala Pro Glu Gly Gly Lys
            20
```

<210> SEQ ID NO 124
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Succinate
<220> FEATURE:
<221> NAME/KEY: SITE
<222> LOCATION: (4)..(13)
<223> OTHER INFORMATION: Cyclic
<220> FEATURE:
<221> NAME/KEY: MOD_RES
<222> LOCATION: (13)..(13)
<223> OTHER INFORMATION: 2,3-diaminopropionic acid
<220> FEATURE:
<223> OTHER INFORMATION: C-term Amide

<400> SEQUENCE: 124

```
Tyr Trp Arg Asp Val Trp Phe Pro His Ala Gln Gly Xaa Val Ala Thr
1               5                   10                  15

Ala Pro Glu Gly Gly Lys
            20
```

<210> SEQ ID NO 125
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: SITE
<222> LOCATION: (4)..(13)
<223> OTHER INFORMATION: Cyclic
<220> FEATURE:
<221> NAME/KEY: MOD_RES
<222> LOCATION: (13)..(13)
<223> OTHER INFORMATION: 2,3-diaminopropionic acid
<220> FEATURE:
<223> OTHER INFORMATION: C-term Amide

<400> SEQUENCE: 125

Tyr Trp Arg Asp Val Trp Phe Pro His Ala Gln Gly Xaa Val Ala Thr
1 5 10 15

Ala Pro Glu Gly Gly Lys
20

<210> SEQ ID NO 126
<211> LENGTH: 21
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: N-term 3-(4-hydroxyphenyl)propionate
<220> FEATURE:
<221> NAME/KEY: SITE
<222> LOCATION: (3)..(12)
<223> OTHER INFORMATION: Cyclic
<220> FEATURE:
<221> NAME/KEY: MOD_RES
<222> LOCATION: (12)..(12)
<223> OTHER INFORMATION: 2,3-diaminopropionic acid
<220> FEATURE:
<223> OTHER INFORMATION: C-term Amide

<400> SEQUENCE: 126

Trp Arg Asp Val Trp Phe Pro His Ala Gln Gly Xaa Val Ala Thr Ala
1 5 10 15

Pro Glu Gly Gly Lys
20

<210> SEQ ID NO 127
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 127

Gly Gly Gly Gly Gly
1 5

<210> SEQ ID NO 128
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 128

Gly Gly Gly Gly Gly Gly Gly Gly
1 5

AFFINITY AGENTS

CROSS REFERENCE TO RELATED APPLICATIONS

This application is a U.S. national stage filing under 35 U.S.C. § 371 of International Application No. PCT/US2022/019839, filed Mar. 10, 2022, which claims the benefit of and priority under 35 U.S.C. § 119 to U.S. Provisional Application No. 63/159,336 filed on Mar. 10, 2021, the entirety of which applications are incorporated by reference herein for all purposes.

BACKGROUND

The purity of biologically produced therapeutics is tightly scrutinized and regulated by authorities to ensure safety and efficacy. Thus, there remains a need for means to efficiently purify of biologically produced therapeutics to a high degree of purity.

SUMMARY

To support the clinical efforts for advanced therapy medicinal products (ATMPs), compositions and methods to efficiently purify ATMPs from recombinant sources are needed. Affinity purification is a means to isolate and/or achieve desired purity of a protein in few steps, or a single step. However, the development of affinity agents (e.g., comprising an affinity ligand) can be a resource intensive and time consuming task and hence affinity agents exist for very few proteins. In the absence of an affinity agent, purification typically involves inefficient processes, such as a multi-column process.

Exosomes are an emerging ATMP with great therapeutic potential (Madhusoodanan 2020). They are a sub-class of extracellular vesicles, which also includes microvesicles and apoptopic bodies (Zaborowski et al. 2015). The manufacturing of exosomes for therapeutic purposes is difficult and expensive. Cell culture productivity is low and typically achieves $10^{11}$-$10^{14}$ exosomes per liter. Purification is mainly accomplished with ion-exchange chromatography. However, this method is not selective for exosomes, hence, resulting in co-purification with other extracellular vesicles and insufficiently clears host cell protein. Thus, there remains a need to selectively purify exosomes.

Given the acknowledged ability of affinity purification to selectively purify targets, there exists a need for affinity agents that meets the rigor of modern bioprocessing. Immunoaffinity, i.e. the use of antibodies as affinity ligands, has demonstrated the requisite selectivity for purification of exosomes (Kowal et al. 2016). The antibodies bind selectively to surface markers that are characteristic of exosomes, the tetraspanins, CD9, CD63 and CD81. However, antibodies are inappropriate for bioprocessing and/or lacking sufficient stability to be compatible with sanitization and cleaning agents. Thus, there exists a need for bioprocess suitable affinity agents.

Affinity agents that bind exosomes and are useful for isolation and/or affinity purification are described herein.

In some embodiments, provided herein are affinity agents comprising cyclic peptides, further comprising an amino acid sequence of SEQ ID NO: 1,

SEQ ID NO: 1:
$X^1YWRB^1VWFPHAQGB^2VX^2\ X^2$ where $X^1$ represents H or N, $X^2$ represents S or T and $B^1$ and $B^2$ represent units through which the peptide is cyclized.

In some embodiments, affinity agents comprise a ligand comprising at least one amino acid sequence shown in Table 5, e.g., any one of SEQ ID NOs: 2-126.

In some embodiments, provided herein are affinity agents comprising at least one ligand comprising an amino acid sequence of SEQ ID NO: 1 that binds to CD81.

In some embodiments, provided herein are affinity agents comprising at least one ligand comprising an amino acid sequence of SEQ ID NO: 1 that binds to exosomes.

In some embodiments, provided herein are affinity agents comprising at least one ligand comprising an amino acid sequence of SEQ ID NO: 1, or an amino acid sequence that differs by no more than three, by no more than two, or by no more than one, substitutions, additions, or deletions.

In some embodiments, provided herein are affinity agents that comprise a plurality of affinity ligands.

In some embodiments, provided herein are affinity agents used for purification of exosomes.

DEFINITIONS

In order for the present disclosure to be more readily understood, certain terms are defined below. Unless defined otherwise herein, technical and scientific terms have the same meaning as commonly understood by one of ordinary skill in the art.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: As used herein, the term "biologically active" refers to a characteristic of any agent that has activity in a biological system, and particularly in an organism. For instance, an agent that, when administered to an organism, has a biological effect on that organism, is considered to be biologically active.

Conservative and non-conservative substitution: A "conservative" amino acid substitution is one in which one amino acid residue is replaced with another amino acid residue having a similar side chain. Families of amino acid residues having similar side chains have been defined in the art, including basic side chains (e.g., lysine (K), arginine (R), histidine (H)); acidic side chains (e.g., aspartic acid (D), glutamic acid (E)); uncharged polar side chains (e.g., glycine (G); asparagine (N), glutamine (Q), serine (S), threonine (T), tyrosine (Y), cysteine (C)); nonpolar side chains (e.g., alanine (A), valine (V), leucine (L), isoleucine (I), proline (P), phenylalanine (F), methionine (M), tryptophan (W), beta-branched side chains (e.g., threonine (T), valine (V), isoleucine (I)); and aromatic side chains (e.g., tyrosine (Y), phenylalanine (F), tryptophan (W), histidine (H)). For example, substitution of a phenylalanine for a tyrosine is a conservative substitution. In some embodiments, conservative amino acid substitutions in the sequence of a ligand confer or improve specific binding of the ligand a target of interest. In some embodiments, conservative amino acid substitutions in the sequences of a ligand do not reduce or abrogate the binding of the ligand to a target of interest. In some embodiments, conservative amino acid substitutions do not significantly affect specific binding of a ligand to a target of interest. Methods of identifying nucleotide and amino acid conservative substitutions and non-conservative substitutions which confer, alter or maintain selective binding affinity are known in the art (see, e.g., Brummell, Biochem. 32:1180-1187 (1993); Kobayashi, *Protein Eng.* 12(10):879-884 (1999); and Burks, *PNAS* 94:412-417 (1997)). In some embodiments, non-conservative amino acid substitutions in the sequence of a ligand confer or improve specific binding of the ligand a target of interest. In some embodiments, non-conservative amino acid substitutions in the sequences of a ligand do not reduce or abrogate the binding of the ligand to a target of interest. In some embodiments, non-conservative amino acid substitutions do not significantly affect specific binding of a ligand to a target of interest.

Linker: As used herein a "linker" refers to a peptide or other chemical linkage that functions to link otherwise independent functional domains. In some embodiments, a linker is located between a ligand and another polypeptide component containing an otherwise independent functional domain. In some embodiments, a linker is a peptide or other chemical linkage located between a ligand and a surface.

Naturally occurring: The term "naturally occurring" when used in connection with biological materials such as a nucleic acid molecules, polypeptides, and host cells, refers to those which are found in nature and not modified by a human being. Conversely, "non-natural" or "synthetic" when used in connection with biological materials refers to those which are not found in nature and/or have been modified by a human being.

"Non-natural amino acids," "amino acid analogs" and "non-standard amino acid residues" are used interchangeably herein. Non-natural amino acids that can be substituted in a ligand as provided herein are known in the art. In some embodiments, a non-natural amino acid is 4-hydroxyproline which can be substituted for proline; 5-hydroxylysine which can be substituted for lysine; 3-methylhistidine which can be substituted for histidine; homoserine which can be substituted for serine; and ornithine which can be substituted for lysine. Additional examples of non-natural amino acids that can be substituted in a polypeptide ligand include, but are not limited to molecules such as: D-isomers of the common amino acids, 2,4-diaminobutyric acid, alpha-amino isobutyric acid, A-aminobutyric acid, Abu, 2-amino butyric acid, gamma-Abu, epsilon-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, beta-alanine, lanthionine, dehydroalanine, γ-aminobutyric acid, selenocysteine and pyrrolysine fluoro-amino acids, designer amino acids such as beta-methyl amino acids, C alpha-methyl amino acids, and N alpha-methyl amino acids.

"Polynucleotide" and "nucleic acid molecule": As used interchangeably herein, polynucleotide and nucleic acid molecule refer to a polymeric form of nucleotides of any length, either ribonucleotides or deoxyribonucleotides. These terms include, but are not limited to, DNA, RNA, cDNA (complementary DNA), mRNA (messenger RNA), IRNA (ribosomal RNA), shRNA (small hairpin RNA), snRNA (small nuclear RNA), snoRNA (short nucleolar RNA), miRNA (microRNA), genomic DNA, synthetic DNA, synthetic RNA, and/or tRNA.

Operably linked: The term "operably linked," as used herein, indicates that two molecules are attached so as to each retain functional activity. Two molecules are "operably linked" whether they are attached directly or indirectly.

Peptide tag: The term "peptide tag" as used herein refers to a peptide sequence that is part of or attached (for instance through genetic engineering) to another protein, to provide a function to the resultant fusion. Peptide tags are usually relatively short in comparison to a protein to which they are fused. In some embodiments, a peptide tag is four or more amino acids in length, such as, 5, 6, 7, 8, 9, 10, 15, 20, or 25 or more amino acids. In some embodiments, a ligand is a protein that contains a peptide tag. Numerous peptide tags that have uses as provided herein are known in the art. Examples of peptide tags that may be a component of a ligand fusion protein or a target bound by a ligand (e.g., a ligand fusion protein) include but are not limited to HA (hemagglutinin), c-myc, the Herpes Simplex virus glycoprotein D (gD), T7, GST, GFP, MBP, Strep-tags, His-tags, Myc-tags, TAP-tags and FLAG tag (Eastman Kodak, Rochester, N. Y.) Likewise, antibodies to the tag epitope allow detection and localization of the fusion protein in, for example, affinity purification, Western blots, ELISA assays, and immunostaining of cells.

Polypeptide: The term "polypeptide" as used herein refers to a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond. As is known to those skilled in the art, polypeptides may be processed and/or modified.

Protein: The term "protein" as used herein refers to one or more polypeptides that function as a discrete unit. If a single polypeptide is the discrete functioning unit and does not require permanent or temporary physical association with other polypeptides in order to form the discrete functioning unit, the terms "polypeptide" and "protein" may be used interchangeably. If the discrete functional unit is comprised of more than one polypeptide that physically associate with one another, the term "protein" refers to the multiple polypeptides that are physically coupled and function together as the discrete unit.

Specifically binds: As used herein in reference to ligands, the term "specifically binds" or "has selective affinity for" means a ligand reacts or associates more frequently, more rapidly, with greater duration, with greater affinity, or combinations of the above to a particular epitope, protein, or target molecule than with alternative substances, including unrelated proteins. Because of the sequence identity between homologous proteins in different species, specific binding can include a binding agent that recognizes a protein or target in more than one species. Likewise, because of homology within certain regions of polypeptide sequences of different proteins, specific binding can include a binding agent that recognizes more than one protein or target. It is understood that, in certain embodiments, a binding agent that specifically binds a first target may or may not specifically bind a second target. As such, "specific binding" does not necessarily require (although it can include) exclusive binding, i.e. binding to a single target. Thus, a ligand or affinity agent may, in certain embodiments, specifically bind more than one target. In certain embodiments, multiple targets may be bound by the same antigen-binding site on an affinity agent.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

DETAILED DESCRIPTION

Figure 1:
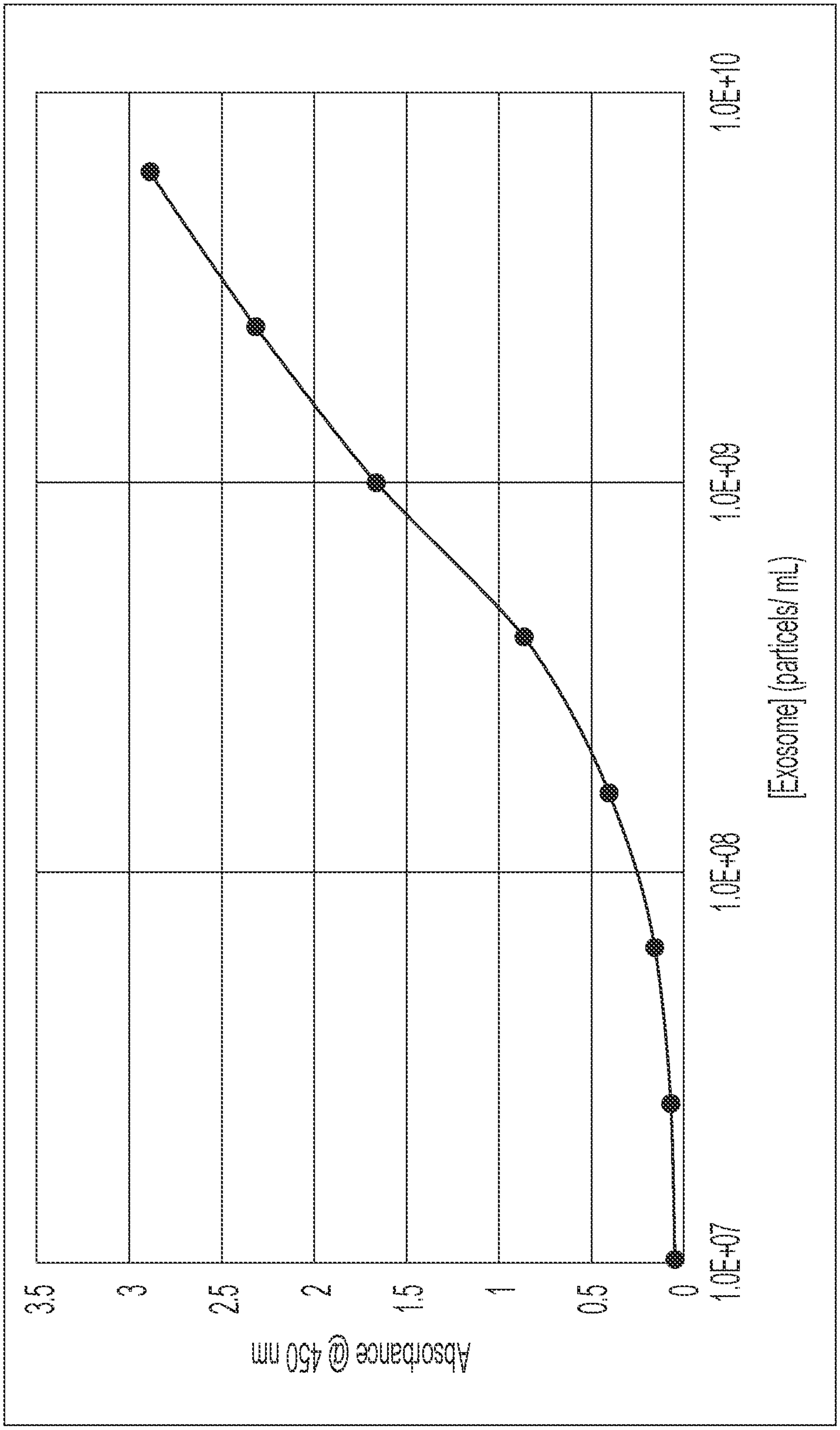
FIG. 1 shows a typical standard curve obtained for CD81 ELISA.

The present disclosure encompasses, inter alia, the recognition that affinity agents prepared from identified and characterized peptide ligands are shown to generate highly purified preparations of one or more targets of interest, for example, in some embodiments, virus particles. In some embodiments, affinity resins described herein are useful for, inter alia, removal protein product related impurities as well as the host cell derived contaminants.

Ligand Binding to Targets of Interest for Use in an Affinity Agent

The characteristics of a ligand binding to a target can be determined using known or modified assays, bioassays, and/or animal models known in the art for evaluating such activity.

As used herein, terms such as "binding affinity for a target", "binding to a target" and the like refer to a property of a ligand which may be directly measured, for example, through the determination of affinity constants (e.g., the amount of ligand that associates and dissociates at a given antigen concentration). Several methods are available to characterize such molecular interactions, for example, competition analysis, equilibrium analysis and microcalorimetric analysis, and real-time interaction analysis based on surface plasmon resonance interaction (for example using a BIACORE instrument). These methods are well-known to those of skill in the art and are discussed in publications such as Neri D et al. (1996) *Tibtech* 14:465-470 and Jansson M et al. (1997) *J Biol Chem* 272:8189-8197.

Affinity requirements for a given ligand binding event are contingent on a variety of factors including, but not limited to: the composition and complexity of the binding matrix, the valency and density of both the ligand and target molecules, and the functional application of the ligand. In some embodiments, a ligand binds a target of interest with a dissociation constant ($K_D$) of less than or equal to $5\times10^{-3}$ M, $10^{-3}$ M, $5\times10^{-4}$ M, $10^{-4}$ M, $5\times10^{-5}$ M, or $10^{-5}$ M. In some embodiments, a ligand binds a target of interest with a $K_D$ of less than or equal to $5\times10^{-6}$ M, $10^{-6}$ M, $5\times10^{-7}$ M, $10^{-7}$ M, $5\times10^{-8}$ M, or $10^{-8}$ M. In some embodiments, a ligand binds a target of interest with a $K_D$ less than or equal to $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M. some embodiments, a ligand generated by methods disclosed herein has a dissociation constant of from about $10^{-4}$ M to about $10^{-5}$ M, from about $10^{-5}$ M to about $10^{-6}$ M, from about $10^{-6}$ M to about $10^{-7}$ M, from about $10^{-7}$ M to about $10^{-8}$ M, from about $10^{-8}$ M to about $10^{-9}$ M, from about $10^{-9}$ M to about $10^{-10}$ M, from about $10^{-10}$ M to about $10^{-11}$ M, or from about $10^{-11}$ M to about $10^{-12}$ M.

Binding experiments to determine $K_D$ and off-rates can be performed in a number of conditions. The buffers in which to make these solutions can readily be determined by one of skill in the art, and depend largely on the desired pH of the final solution. Low pH solutions (<pH 5.5) can be made, for example, in citrate buffer, glycine-HCl buffer, or in succinic acid buffer. High pH solutions can be made, for example, in Tris-HCl, phosphate buffers, or sodium bicarbonate buffers. A number of conditions may be used to determine $K_D$ and off-rates for the purpose of determining, for example, optimal pH and/or salt concentrations.

In some embodiments, a ligand specifically binds a target of interest with a $k_{off}$ ranging from 0.1 to $10^{-7}$ $sec^{-1}$, $10^{-2}$ to $10^{-7}$ $sec^{-1}$, or $0.5\times10^{-2}$ to $10^{-7}$ $sec^{-1}$. In some embodiments, a ligand binds a target of interest with an off rate ($k_{off}$) of less than $5\times10^{-2}$ $sec^{-1}$, $10^{-2}$ $sec^{-1}$, $5\times10^{-3}$ $sec^{-1}$, or $10^{-3}$ $sec^{-1}$ In some embodiments a ligand binds a target of interest with an off rate ($k_{off}$) of less than $5\times10^{-4}$ $sec^{-1}$, $10^{-4}$ $sec^{-1}$, $5\times10^{-5}$ $sec^{-1}$, or $10^{-5}$ $sec^{-1}$, $5\times10^{-6}$ $sec^{1}$, $10^{-6}$ $sec^{-1}$, $5\times10^{-7}$ $sec^{-1}$, or $10^{-7}$ $sec^{-1}$.

In some embodiments, a ligand specifically binds a target of interest with a $k_{on}$ ranging from about $10^3$ to $10^7$ $M^{-1}sec^{-1}$, $10^3$ to $10^6$ $M^{-1}sec^{-1}$, or $10^3$ to $10^5$ $M^{-1}sec^{-1}$. In some embodiments, a ligand (e.g., a ligand fusion protein) binds the target of interest with an on rate ($k_{on}$) of greater than $10^3$ $M^{-1}sec^{-1}$, $5\times10^3$ $M^{-1}sec^{-1}$, $10^4$ $M^{-1}sec^{-1}$, or $5\times10^4$ $M^{-1}sec^{-1}$. In an additional embodiment, a ligand, binds a target of interest with a $k_{on}$ of greater than $10^5$ $M^{-1}sec^{-1}$, $5\times10^5$ $M^{-1}sec^{-1}$, $10^6$ $M^{-1}sec^{-1}$, $5\times10^6$ $M^{-1}sec^{-1}$, or $10^7$ $M^{-1}sec^{-1}$.

Targets of Interest

In accordance with various embodiments, a target of interest specifically bound by a ligand can be any molecule for which it is desirable for a ligand of an affinity agent to bind. For example, a target specifically bound by ligand can be any target of purification, manufacturing, formulation, therapeutic, diagnostic, or prognostic relevance or value. Non-limiting uses include therapeutic and diagnostic uses. A number of exemplary targets are provided herein, by way of example, and are intended to be illustrative and not limiting. A target of interest can be naturally occurring or synthetic. In some embodiments, a target is AAV2 and/or variants derived from AAV2.

Linkers

The terms "linker" and "spacer" are used interchangeably herein to refer to a peptide or other chemical linkage that functions to link otherwise independent functional domains. In some embodiments, a linker is located between a ligand and another polypeptide component containing an otherwise independent functional domain. Suitable linkers for coupling two or more linked ligands may generally be any linker used in the art to link peptides, proteins or other organic molecules. In some embodiments, such a linker is suitable for constructing proteins or polypeptides that are intended for pharmaceutical use.

Suitable linkers for operably linking a ligand and an additional component of a ligand fusion protein in a single-chain amino acid sequence include but are not limited to, polypeptide linkers such as glycine linkers, serine linkers, mixed glycine/serine linkers, glycine- and serine-rich linkers or linkers composed of largely polar polypeptide fragments.

In some embodiments, a linker comprises a majority of amino acids selected from glycine, alanine, proline, asparagine, glutamine, and lysine. In some embodiments, a linker comprises a majority of amino acids selected from glycine, alanine, proline, asparagine, aspartic acid, threonine, glutamine, and lysine. In some embodiments, a ligand linker is made up of a majority of amino acids that are sterically unhindered. In some embodiments, a linker comprises a majority of amino acids selected from glycine, serine, and/or alanine. In some embodiments, a peptide linker is selected from polyglycines (such as $(Gly)_5$, and $(Gly)_8$, poly(Gly-Ala), and polyalanines.

Linkers can be of any size or composition so long as they are able to operably link a ligand in a manner that permits the ligand to bind a target of interest. In some embodiments, linkers are from about 1 to 50 amino acids, from about 1 to 20 amino acids, from about 1 to 15 amino acids, from about 1 to 10 amino acids, from about 1 to 5 amino acids, from about 2 to 20 amino acids, from about 2 to 15 amino acids, from about 2 to 10 amino acids, or from about 2 to 5 amino acids. It should be clear that the length, the degree of flexibility and/or other properties of the linker(s) may influence certain properties of a ligand for use in an affinity agent, such as affinity, specificity or avidity for a target of interest, or for one or more other target proteins of interest, or for proteins not of interest (i.e., non-target proteins). In some embodiments, two or more linkers are utilized. In some embodiments, two or more linkers are the same. In some embodiments, two or more linkers are different.

In some embodiments, a linker is a non-peptide linker such as an alkyl linker, or a PEG linker. For example, alkyl linkers such as —NH—(CH2)s-C(O)—, wherein s=2-20 can be used. These alkyl linkers may further be substituted by any non-sterically hindering group such as lower alkyl e.g., C1 C6) lower acyl, halogen (e.g., CI, Br), CN, NH2, phenyl, etc. An exemplary non-peptide linker is a PEG linker. In some embodiments, a PEG linker has a molecular weight of from about 100 to 5000 kDa, or from about 100 to 500 kDa.

Linkers can be evaluated using techniques described herein and/or otherwise known in the art. In some embodiments, linkers do not alter (e.g., do not disrupt) the ability of a ligand to bind a target molecule.

Affinity Agents Comprising Conjugated Ligands

Ligands that promote specific binding to targets of interest can be chemically conjugated with a variety of chromatography compositions (e.g., beads, resins, gels, membrane, monoliths, etc.) to prepare an affinity agent. Affinity agents comprising ligands are particularly useful for purification and manufacturing applications.

In some embodiments, a ligand (e.g., a ligand fusion protein) comprises or contains at least one reactive residue. Reactive residues are useful, for example, as sites for the attachment of conjugates such as chemotherapeutic drugs. An exemplary reactive amino acid residue is lysine. A reactive residue (e.g., lysine) can be added to a ligand at either end, or within the ligand sequence and/or can be substituted for another amino acid in the sequence of a ligand. A suitable reactive residue (e.g., lysine, etc.) can also be located within the sequence of an identified ligand without need for addition or substitution. An additional exemplary reactive amino acid residue is cysteine.

Attachment to Solid Surface

"Solid surface," "support," or "matrix" are used interchangeably herein and refer to, without limitation, any column (or column material), bead, test tube, microtiter dish, solid particle (for example, agarose or sepharose), microchip (for example, silicon, silicon-glass, or gold chip), or membrane (synthetic (e.g. a filter) or biological (e.g. liposome or vesicle) in origin) to which a ligand, affinity agent, antibody, or other protein may be attached (i.e., coupled, linked, or adhered), either directly or indirectly (for example, through other binding partner intermediates such as other antibodies or Protein A), or in which a ligand or antibody may be embedded (for example, through a receptor or channel). Reagents and techniques for attaching polypeptides to solid supports (e.g, matrices, resins, plastic, etc.) are well-known in the art. Suitable solid supports include, but are not limited to, a chromatographic resin or matrix (e.g., SEPHAROSE-4 FF agarose beads), the wall or floor of a well in a plastic microtiter dish, a silica based biochip, polyacrylamide, agarose, silica, nitrocellulose, paper, plastic, nylon, metal, and combinations thereof. Ligands and other compositions may be attached on a support material by a non-covalent association or by covalent bonding, using reagents and techniques known in the art. In some embodiments, a ligand is coupled to a chromatography material using a linker.

Production of Ligands

The production of a ligand, useful in practicing several embodiments of provided methods, may be carried out using a variety of standard techniques for chemical synthesis, semi-synthetic methods, and recombinant DNA methodologies known in the art. Also provided are methods for producing a ligand, individually or as part of multi-domain fusion protein, as soluble agents and cell associated proteins. In some embodiments, the overall production scheme for a ligand comprises obtaining a reference protein scaffold and identifying a plurality of residues within the scaffold for modification. Depending on the embodiment, the reference scaffold may comprise a protein structure with one or more alpha-helical regions, or other tertiary structure. Once identified, any of a plurality of residues can be modified, for example by substitution of one or more amino acids. In some embodiments, one or more conservative substitutions are made. In some embodiments, one or more non-conservative substitutions are made. In some embodiments, a natural amino acid (e.g., one of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine) is substituted into a reference scaffold at targeted positions for modification. In some embodiments, modifications do not include substituting in either a cysteine or a proline. After modifications have been made at identified positions desired in a particular embodiment, the resulting modified polypeptides (e.g., candidate ligands) can be recombinantly expressed, for example in a plasmid, bacteria, phage, or other vector (e.g. to increase the number of each of the modified polypeptides). The modified polypeptides can then be purified and screened to identify those modified polypeptides that have specific binding to a particular target of interest. Modified polypeptides may show enhanced binding specificity for a target of interest as compared to a reference scaffold, or may exhibit little or no binding to a given target of interest (or to a non-target protein). In some embodiments, depending on the target of interest, a reference scaffold may show some interaction (e.g. nonspecific interaction) with a target of interest, while certain modified polypeptides will exhibit at least about two fold, at least about five fold, at least about 10 fold, at least about 20 fold, at least about 50 fold, or at least about 100 fold (or more) increased binding specificity for a target of interest. Additional details regarding production, selection, and isolation of ligand are provided in more detail below.

Recombinant Expression of Ligands

In some embodiments, a ligand such as a ligand fusion protein is "recombinantly produced," (i.e., produced using recombinant DNA technology). Exemplary recombinant methods available for synthesizing ligands (e.g., ligand fusion proteins), include, but are not limited to polymerase chain reaction (PCR) based synthesis, concatemerization, seamless cloning, and recursive directional ligation (RDL) (see, e.g., Meyer et al., *Biomacromolecules* 3:357-367 (2002), Kurihara et al., *Biotechnol. Lett.* 27:665-670 (2005), Haider et al., *Mol. Pharm.* 2:139-150 (2005); and McMillan et al., *Macromolecules* 32(11):3643-3646 (1999).

Nucleic acids comprising a polynucleotide sequence encoding a ligand are also provided. Such polynucleotides optionally further comprise one or more expression control elements. For example, a polynucleotide can comprise one or more promoters or transcriptional enhancers, ribosomal binding sites, transcription termination signals, and polyadenylation signals, as expression control elements. A polynucleotide can be inserted within any suitable vector, which can be contained within any suitable host cell for expression.

Expression of nucleic acids encoding ligands is typically achieved by operably linking a nucleic acid encoding the ligand to a promoter in an expression vector. Typical expression vectors contain transcription and translation terminators, initiation sequences, and promoters useful for regulation of the expression of the desired nucleic acid sequence. Exemplary promoters useful for expression in *E. coli* include, for example, the T7 promoter.

Methods known in the art can be used to construct expression vectors containing the nucleic acid sequence encoding a ligand along with appropriate transcriptional/translational control signals. These methods include, but are not limited to in vitro recombinant DNA techniques, synthetic techniques and in vivo recombination/genetic recombination. Expression of a polynucleotide can be performed in any suitable expression host known in the art including, but not limited to, bacterial cells, yeast cells, insect cells, plant cells or mammalian cells. In some embodiments, a nucleic acid sequence encoding a ligand is operably linked to a suitable promoter sequence such that a nucleic acid sequence is transcribed and/or translated into ligand in a host.

A variety of host-expression vector systems can be utilized to express a nucleic acid encoding a ligand. Vectors containing the nucleic acids encoding a ligand (e.g., individual ligand subunits or ligand fusions) or portions or fragments thereof, include plasmid vectors, a single and double-stranded phage vectors, as well as single and double-stranded RNA or DNA viral vectors. Phage and viral vectors may also be introduced into host cells in the form of packaged or encapsulated virus using known techniques for infection and transduction. Moreover, viral vectors may be replication competent or alternatively, replication defective. Alternatively, cell-free translation systems may also be used to produce the protein using RNAs derived from the DNA expression constructs (see, e.g., WO86/05807 and WO89/01036; and U.S. Pat. No. 5,122,464).

Generally, any type of cell or cultured cell line can be used to express a ligand provided herein. In some embodiments a background cell line used to generate an engineered host cell is a phage, a bacterial cell, a yeast cell or a mammalian cell. A variety of host-expression vector systems may be used to express a nucleic acid sequence encoding a ligand or a ligand fusion protein. Mammalian cells can be used as host cell systems transfected with recombinant plasmid DNA or cosmid DNA expression vectors comprising or containing a nucleic acid sequence encoding a target of interest and a nucleic acid sequence encoding a polypeptide or a fusion polypeptide. The cells can be primary isolates from organisms, cultures, or cell lines of transformed or transgenic nature.

Suitable host cells include but are not limited to microorganisms such as, bacteria (e.g., *E. coli, B. subtilis*) transformed with recombinant bacteriophage DNA, plasmid DNA or cosmid DNA expression vectors containing ligand coding sequences; yeast (e.g., Saccharomyces, Pichia) transformed with recombinant yeast expression vectors containing ligand coding sequences; insect cell systems infected with recombinant virus expression vectors (e.g., Baculovirus) containing ligand coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing ligand coding sequences.

Prokaryotes useful as host cells in producing a ligand include gram negative or gram positive organisms such as, *E. coli* and *B. subtilis*. Expression vectors for use in prokaryotic host cells generally contain one or more phenotypic selectable marker genes (e.g., genes encoding proteins that confer antibiotic resistance or that supply an autotrophic requirement). Examples of useful prokaryotic host expression vectors include the pKK223-3 (Pharmacia, Uppsala, Sweden), pGEMI (Promega, Wis., USA), pET (Novagen, Wis., USA) and pRSET (Invitrogen, Calif., USA) series of vectors (see, e.g., Studier, J. Mol. Biol. 219:37 (1991) and Schoepfer, *Gene* 124:83 (1993)). Exemplary promoter sequences frequently used in prokaryotic host cell expression vectors include T7, (Rosenberg et al., *Gene* 56:125-135 (1987)), beta-lactamase (penicillinase), lactose promoter system (Chang et al., *Nature* 275:615 (1978)); and Goeddel et al., *Nature* 281:544 (1979)), tryptophan (trp) promoter system (Goeddel et al., *Nucl. Acids Res.* 8:4057, (1980)), and tac promoter (Sambrook et al., 1990, Molecular Cloning, A Laboratory Manual, 2d Ed., Cold Spring Harbor Laboratory, Cold Spring Harbor, N.Y.).

In some embodiments, a eukaryotic host cell system is used, including yeast cells transformed with recombinant yeast expression vectors comprising or containing a nucleic acid sequence encoding a ligand. Exemplary yeast that can be used to produce compositions of the invention, include yeast from the genus Saccharomyces, Pichia, Actinomycetes and Kluyveromyces. Yeast vectors typically contain an origin of replication sequence from a 2 mu yeast plasmid, an autonomously replicating sequence (ARS), a promoter region, sequences for polyadenylation, sequences for transcription termination, and a selectable marker gene. Examples of promoter sequences in yeast expression constructs include, promoters from metallothionein, 3-phosphoglycerate kinase (Hitzeman, *J. Biol. Chem.* 255:2073 (1980)) and other glycolytic enzymes, such as, enolase, glyceraldehyde-3-phosphate dehydrogenase, hexokinase, pyruvate decarboxylase, phosphofructokinase, glucose-6-phosphate isomerase, 3-phospho glycerate mutase, pyruvate kinase, triosephosphate isomerase, phosphoglucose isomerase, and glucokinase. Additional suitable vectors and promoters for use in yeast expression as well as yeast transformation protocols are known in the art. See, e.g., Fleer, *Gene* 107:285-195 (1991) and Hinnen, *PNAS* 75:1929 (1978).

Insect and plant host cell culture systems are also useful for producing ligands described herein. Such host cell systems include for example, insect cell systems infected with recombinant virus expression vectors (e.g., baculovirus) comprising or containing a nucleic acid sequence encoding a ligand; plant cell systems infected with recombinant virus expression vectors (e.g., cauliflower mosaic virus, CaMV; tobacco mosaic virus, TMV) or transformed with recombinant plasmid expression vectors (e.g., Ti plasmid) comprising or containing a nucleic acid sequence encoding a ligand, including, but not limited to, the expression systems taught in U.S. Pat. No. 6,815,184; U.S. Publ. Nos. 60/365,769, and 60/368,047; and WO2004/057002, WO2004/024927, and WO2003/078614.

In some embodiments, host cell systems may be used, including animal cell systems infected with recombinant virus expression vectors (e.g., adenoviruses, retroviruses, adeno-associated viruses, herpes viruses, lentiviruses) including cell lines engineered to contain multiple copies of the DNA encoding a ligand either stably amplified (CHO/dhfr) or unstably amplified in double-minute chromosomes (e.g., murine cell lines). In some embodiments, a vector comprising a polynucleotide(s) encoding a ligand is polycistronic. Exemplary mammalian cells useful for producing these compositions include 293 cells (e.g., 293T and 293F), CHO cells, BHK cells, NS0 cells, SP2/0 cells, YO myeloma cells, P3X63 mouse myeloma cells, PER cells, PER.C6 (Crucell, Netherlands) cells VERY, Hela cells, COS cells, MDCK cells, 3T3 cells, W138 cells, BT483 cells, Hs578T cells, HTB2 cells, BT20 cells, T47D cells, CRL7O30 cells, HsS78Bst cells, hybridoma cells, and other mammalian cells. Additional exemplary mammalian host cells that are useful in practicing the invention include but are not limited, to T cells. Exemplary expression systems and selection methods are known in the art and, including those described in the following references and references cited therein: Borth et al., *Biotechnol. Bioen.* 71(4):266-73 (2000), in Werner et al., *Arzneimittelforschung Drug Res.* 48(8):870-80 (1998), Andersen et al., *Curr. Op. Biotechnol.* 13:117-123 (2002), Chadd et al., *Curr. Op, Biotechnol.* 12:188-194 (2001), and Giddings, Curr. Op. Biotechnol. 12:450-454 (2001). Additional examples of expression systems and selection methods are described in Logan et al., *PNAS* 81:355-359 (1984), Birtner et al. *Methods Enzymol.* 153:51-544 (1987)). Transcriptional and translational control sequences for mammalian host cell expression vectors are frequently derived from viral genomes. Commonly used promoter sequences and enhancer sequences in mammalian expression vectors include, sequences derived from Polyoma virus, Adenovirus 2, Simian Virus 40 (SV40), and human cytomegalovirus (CMV). Exemplary commercially available expression vectors for use in mammalian host cells include pCEP4 (Invitrogen) and pcDNA3 (Invitrogen).

Physical methods for introducing a nucleic acid into a host cell (e.g., a mammalian host cell) include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York).

Biological methods for introducing a polynucleotide of interest into a host cell include the use of DNA and RNA vectors. Viral vectors, and especially retroviral vectors, have become the most widely used method for inserting genes into mammalian (e.g., human) cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Methods for introducing a DNA and RNA polynucleotides of interest into a host cell include electroporation of cells, in which an electrical field is applied to cells in order to increase permeability of a cell membrane, allowing chemicals, drugs, or polynucleotides to be introduced into a cell. Ligand containing DNA or RNA constructs may be introduced into mammalian or prokaryotic cells using electroporation.

In some embodiments, electroporation of cells results in expression of a ligand-CAR on a surface of T cells, NK cells, and/or NKT cells. Such expression may be transient or stable over the life of a cell. Electroporation may be accomplished with methods known in the art including MaxCyte GT® and STX® Transfection Systems (MaxCyte, Gaithersburg, MD, USA).

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). In the case where a non-viral delivery system is utilized, an exemplary delivery vehicle may be or comprise a liposome. The use of lipid formulations is contemplated for introduction of nucleic acids into a host cell (in vitro, ex vivo or in vivo). In some embodiments, a nucleic acid is associated with a lipid. A nucleic acid associated with a lipid can be encapsulated in an aqueous interior of a liposome, interspersed within a lipid bilayer of a liposome, attached to a liposome via a linking molecule that is associated with both a liposome and an oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they can be present in a bilayer structure, as micelles, or with a "collapsed" structure. They can also simply be interspersed in a solution, possibly forming aggregates that are not uniform in size or shape. Lipids are fatty substances which can be naturally occurring or synthetic lipids. For example, lipids include fatty droplets that naturally occur in cytoplasm as well as a class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyi phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyi phosphatidylglycerol ("DMPG") and other lipids may be obtained from Avanti Polar Lipids, Inc. (Birmingham, AL). Stock solutions of lipids in chloroform or chloroform/methanol can be stored at about −20 °C. Chloroform may be used as the only solvent since it is more readily evaporated than methanol. "Liposome" is a generic term encompassing a variety of single and multilamellar lipid vehicles formed by generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. Lipid components undergo self-rearrangement before formation of closed structures and entrap water and dissolved solutes between the lipid bilayers (Ghosh et al., *Glycobiology* 5:505-510 (1991)). However, compositions that have different structures in solution than normal vesicular structure are also encompassed. For example, lipids can assume a micellar structure or merely exist as non-uniform aggregates of lipid molecules. Also contemplated are lipofectamine-nucleic acid complexes.

Regardless of the method used to introduce exogenous nucleic acids into a host cell, presence of recombinant nucleic acid sequence in the host cell can routinely be confirmed through a variety of assays known in the art. Such assays include, for example, "molecular biological" assays known in the art, such as Southern and Northern blotting, RT-PCR and PCR; "biochemical" assays, such as detecting presence or absence of a particular peptide, e.g., by immunological means (ELISAs and Western blots) or by assays described herein to identify agents.

Reporter genes are used for identifying potentially transfected cells and for evaluating functionality of regulatory sequences. In general, a reporter gene is a gene that is not present in or expressed by a recipient organism, tissue, or cell and that encodes a polypeptide whose expression is manifested by some easily detectable property, e.g., enzymatic activity. Expression of a reporter gene is assayed at a suitable time after DNA has been introduced into the recipient cells. Suitable reporter genes include, but are not limited to, genes encoding luciferase, beta-galactosidase, chloramphenicol acetyl transferase, secreted alkaline phosphatase, or green fluorescent protein gene (e.g., Ui-Tei et al., *FEBS Lett.* 479:79-82 (2000)). Suitable expression systems are known in the art and can be prepared using known techniques or obtained commercially. In general, construct with a minimal 5' flanking region showing a highest level of expression of reporter gene is identified as a promoter. Such promoter regions can routinely be linked to a reporter gene and used to evaluate agents for ability to modulate promoter-driven transcription.

A number of selection systems can be used in mammalian host-vector expression systems, including, but not limited to, herpes simplex virus thymidine kinase, hypoxanthine-guanine phosphoribosyltransferase and adenine phosphoribosyltransferase (Lowy et al., *Cell* 22:817 (1980)) genes. Additionally, antimetabolite resistance can be used as a basis of selection for e.g., dhfr, gpt, neo, hygro, trpB, hisD, ODC (ornithine decarboxylase), and the glutamine synthase system.

Ligand Purification

Once a ligand or a ligand fusion protein has been produced by recombinant expression, it can be purified by methods known in the art for purification of a recombinant protein, for example, by chromatography (e.g., ion exchange, affinity, and/or sizing column chromatography), centrifugation, differential solubility, or by any other standard technique for the purification of proteins. In some embodiments, a ligand is optionally fused to heterologous polypeptide sequences specifically disclosed herein or otherwise known in the art to facilitate purification. In some embodiments, ligands (e.g., antibodies and other affinity matrices) are for ligand affinity columns and/or for affinity purification and that optionally, a ligand or other components of a ligand fusion composition bound by these ligands are removed from a composition prior to final preparation of a ligand using techniques known in the art.

Chemical Synthesis of Ligand

In addition to recombinant methods, ligand production may also be carried out using organic chemical synthesis of a desired polypeptide using a variety of liquid and solid phase chemical processes known in the art. Various automatic synthesizers are commercially available and can be used in accordance with known protocols. See, for example, Tam et al., *J. Am. Chem. Soc.,* 105:6442 (1983); Merrifield, *Science,* 232:341-347 (1986); Barany and Merrifield, The Peptides, Gross and Meienhofer, eds, Academic Press, New York, 1-284; Barany et al., *Int. J. Pep. Protein Res.,* 30:705 739 (1987); Kelley et al. in Genetic Engineering Principles and Methods, Setlow, J. K., ed. Plenum Press, NY. 1990, vol. 12, pp. 1-19; Stewart et al., Solid-Phase Peptide Synthesis, W.H. Freeman Co., San Francisco, 1989. One advantage of these methodologies is that they allow for incorporation of non-natural amino acid residues into an amino acid sequence of a ligand.

Ligands that are used in the methods of the present invention may be modified during or after synthesis or translation, e.g., by glycosylation, acetylation, benzylation, phosphorylation, amidation, pegylation, formylation, derivatization by known protecting/blocking groups, proteolytic cleavage, linkage to an antibody molecule, hydroxylation, iodination, methylation, myristoylation, oxidation, pegylation, proteolytic processing, phosphorylation, prenylation, racemization, selenoylation, sulfation, ubiquitination, etc. (See, e.g., Creighton, Proteins: Structures and Molecular Properties, 2d Ed. (W.H. Freeman and Co., N.Y., 1992); Postranslational Covalent Modification of Proteins, Johnson, ed. (Academic Press, New York, 1983), pp. 1-12; Seifter, *Meth. Enzymol.,* 182:626-646 (1990); Rattan, *Ann. NY Acad. Sci.,* 663:48-62 (1992).) In some embodiments, ligands are acetylated at the N-terminus and/or amidated at the C-terminus.

Any of numerous chemical modifications may be carried out by known techniques, including, but not limited to acetylation, formylation, etc. Additionally, derivatives may contain one or more non-classical amino acids.

In some embodiments cyclization, or macrocyclization of a peptide backbone is achieved by sidechain to sidechain linkage formation. Methods for achieving this are well known in the art and may involve natural as well as unnatural amino acids. Approaches includes disulfide formation, lanthionine formation or thiol alkylations (e.g. Michael addition), amidation between amino and carboxylate sidechains, click chemistry (e.g. azide-alkyne condensation), peptide stapling, ring closing metathesis and the use of enzymes.

Affinity Agents for Purification

In purification based on affinity chromatography, a target of interest (e.g. protein or molecule) is selectively isolated according to their ability to specifically and reversibly bind to a ligand that has typically been covalently coupled to a chromatographic matrix. In some embodiments, ligands can be used as reagents for affinity purification of targets of interest from either recombinant sources or natural sources such as biological samples (e.g., serum).

In some embodiments, a ligand that specifically binds a target of interest is immobilized on beads and then used to affinity purify the target.

Methods of covalently coupling proteins to a surface are known by those of skill in the art, and peptide tags that can be used to attach ligand to a solid surface are known to those of skill in the art. Further, ligand can be attached (e.g., coupled, linked, and/or adhered) to a solid surface using any reagents or techniques known in the art. In some embodiments, a solid support comprises beads, glass, slides, chips and/or gelatin. Thus, a series of ligands can be used to make an array on a solid surface using techniques known in the art. For example, U.S. Publ. No. 2004/0009530 discloses methods for preparing arrays.

In some embodiments, a ligand is used to isolate a target of interest by affinity chromatography. In some embodiments, a ligand is immobilized on a solid support. The ligand can be immobilized on a solid support using techniques and reagents described herein or otherwise known in the art. Suitable solid supports are described herein or otherwise known in the art and in specific embodiments are suitable for packing a chromatography column. An immobilized ligand can then be loaded or contacted with a solution under conditions favorable to form a complex between the ligand and the target of interest. Non-binding materials can be washed away. Suitable wash conditions can readily be determined by one of skill in the art. Examples of suitable wash conditions are described in Shukla and Hinckley, *Biotechnol Prog.* 2008 September-October; 24(5):1115-21. doi: 10.1002/btpr.50.

In some embodiments, chromatography is carried out by mixing a solution containing a target of interest and a ligand, then isolating complexes of a target of interest and ligand. For example, a ligand is immobilized on a solid support such as beads, then separated from a solution along with a target of interest by filtration. In some embodiments, a ligand is or comprises a fusion protein that contains a peptide tag, such as a poly-HIS tail or streptavidin binding region, which can be used to isolate the ligand after complexes have formed using an immobilized metal affinity chromatographic resin or streptavidin-coated substrate. Once separated, a target of interest can be released from a ligand under elution conditions and recovered in a purified form.

EXAMPLES

Example 1

Peptides were synthesized by standard Fmoc solid phase peptide synthesis techniques and purified by preparative reverse phase HPLC. The purity of peptides was assessed by RP UPLC with both UV and quadrupole time-of-flight mass spectrometric detection.

Example 2

Figure 5:
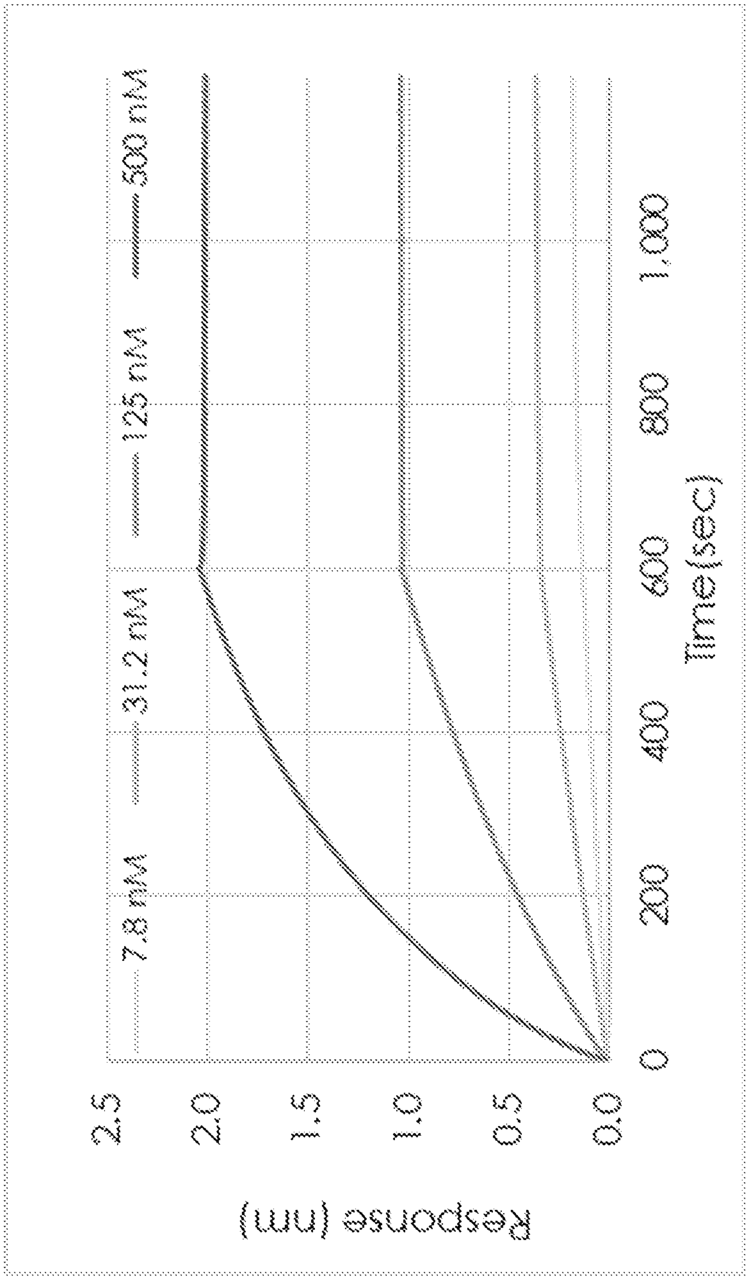
FIG. 5 shows a sensorgram for the binding of Fc-CD81 fusion protein at various concentrations to the immobilized ligand corresponding to SEQ ID NO: 58.
Figure 6:
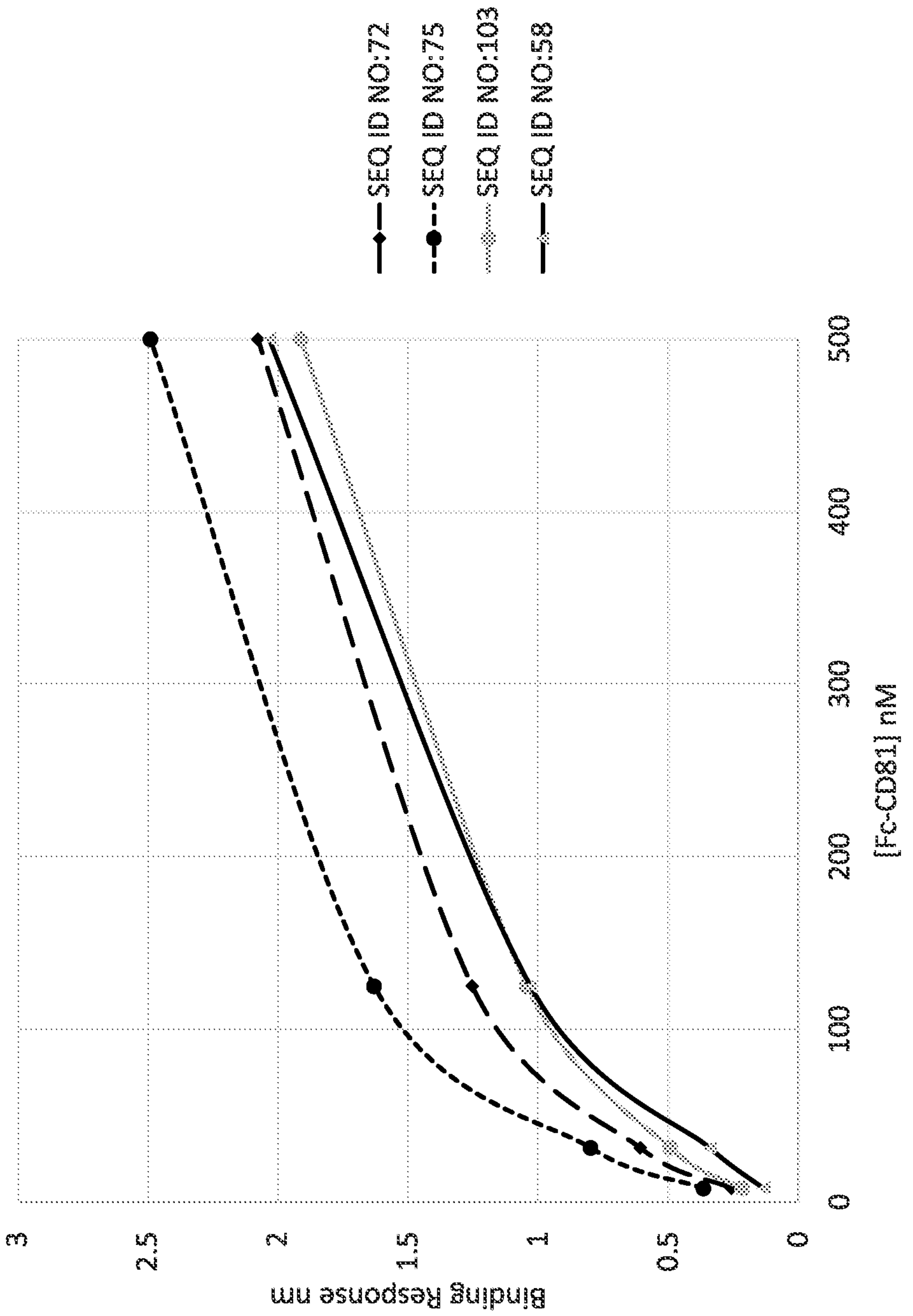
FIG. 6 shows the dose response curves for the binding of several ligands to Fc-CD81.

This example demonstrates the binding of biotinylated ligands to CD81 using biolayer interferometry (ForteBio, Menlo Park, CA). Biotinylated ligands, were immobilized on sensors and incubated with solutions containing different concentrations of Fc-CD81 (R&D Systems, Minneapolis, MN) in PBS containing, 0.01% (w/v) bovine serum albumin and 0.1% (v/v) Tween-20, pH 7.4. A blank sensor was included as a control. An example sensorgram is shown in FIG. 5 and example data shown in FIG. 6.

Example 3

This example describes the assays used to monitor the tetraspanin exosome markers CD9, CD63 and CD81. Reagents for western blotting are shown in Table 1. Gels were blotted onto PVDF membranes and processed with GOBlot processors (Cytoskeleton, Denver, CO). Blots were developed with SuperSignal™ West Pico PLUS Chemiluminescent Substrate (Thermo Scientific, Waltham, MA) and imaged with a BioRad ChemiDoc MP system (BioRad, Hercules, CA).

TABLE 1

| Target Protein | Primary Antibody & Dilution | Secondary Antibody & Dilution |
|---|---|---|
| CD9 | BD Pharmingen 555370 1:1000 | BioRad Goat anti-Mouse HRP 1706516 1:1000 |
| CD63 | NovusBio NBP2-42225 1:1000 | BioRad Goat anti-Mouse HRP 1706516 1:1000 |
| CD81 | Invitrogen MA5-13548 1:1000 | BioRad Goat anti-Mouse HRP 1706516 1:1000 |

CD81 was also assayed by adapting the PS Capture™ Exosome ELISA Kit (Fujifilm, Richmond, VA). An anti-CD81 antibody, MA5-13548 (Invitrogen, Waltham, MA), diluted 1:500 was substituted for the anit-CD63 antibody included in the kit. An example standard curve is shown in FIG. 1.

Example 4

This example demonstrates the production and characterization of affinity agents comprising ligands identified and described herein. Affinity resins were prepared by conjugating aminated ligands to agarose beads. RAPID RUN 6% Agarose beads (ABT, Madrid, Spain) and Praesto® Jetted A50 beads (Purolite, King of Prussia, PA) were activated with disuccinimidyl carbonate and coupled with ligands at ligand densities 1-8 mg/mL resin. The actual ligand density for all resins was measured using a subtractive RP-HPLC method according to the following formula:

Actual Ligand Density=(Measured [ligand] in feed−Measured [ligand] in effluent).

For the preparation of affinity resins with thiolated ligands conjugated to agarose beads, Praesto® Jetted A50 beads (Purolite, King of Prussia, PA) were activated with disuccinimidyl carbonate and coupled with excess ethylenediamine. After washing, bromoacetate was conjugated to the aminated beads using EDC activation. After washing, ligands were conjugated to the beads at room temperature. After washing, the beads were deactivated with excess thioglycerol. Ligand densities were determined as described above.

Example 5

This example demonstrates binding capacity of affinity agents comprising binding ligands described herein for affinity capture of exosomes. A filter plate binding experiment using Durapore Membrane. Cat #MSHVS4510 (Millipore, Burlington MA) was operated as shown in Table 2.

TABLE 2

| Step | Buffer | uL | Time (min) | # of Cycles |
|---|---|---|---|---|
| Pre-block | 1% BSA + 0.002% Tween 20 in PBS | 100 | 15 | 2 |
| Resin addition | Resin slurry in 20% ethanol | 5 (resin) | N/A | 1 |
| Equilibration | PBS + 0.002% Tween 20 | 100 | 2 | 5 |
| Load Sample | 1E10 particles/mL in PBST | 100 | 60 | 1 |
| Wash | PBS + 0.002% Tween 20 | 100 | 5 | 3 |
| Elution | varied | 100 | 10 | 2 |
| Strip | 0.1M NaOH | 100 | 5 | 1 |

Resins were prepared by conjugating ligands to A50 beads. The ligand densities and capture efficiency of each resin is shown in Table 3.

TABLE 3

| SEQ ID No. | Ligand density | Ave Capture (%) |
|---|---|---|
| 28 | 9.8 mg/mL | 97 |
| 28 | 7.7 mg/mL | 38 |
| 43 | 11.2 mg/mL | 98 |
| 43 | 7.4 mg/mL | 89 |
| Blank bead | — | -2 |

Example 6

This example demonstrates the use of affinity agents comprising binding ligands described herein for affinity purification of exosomes. A resin comprising a ligand corresponding to SEQ ID NO: 43 at 11.2 mg/mL ligand density was used to pack a 0.18 mL glass column (3×25 mm) and operated as described in Table 4.

TABLE 4

| Step | Buffer | Volume (mL) | Residence Time (min) | CVs |
|---|---|---|---|---|
| Equilibration | PBS + 0.002% Tween20, pH 7.4 | 5 | 0.9 | 28 |
| Load Sample | Clarified cell supernatant feed | 2 | 3.5 | 11 |
| Chase | PBS + 0.002% Tween20, pH 7.4 | 2 | 3.5 | 11 |
| Wash | PBS + 0.002% Tween20, pH 7.4 | 4 | 0.9 | 23 |
| Elute | 1M L-Arginine, pH 9 | 4 | 0.9 | 23 |
| CIP/Strip | 0.1M NaOH | 4 | 0.9 | 23 |
| Re-Equilibration | PBS + 0.002% Tween20, pH 7.4 | 12 | 0.9 | 68 |

Figure 2:
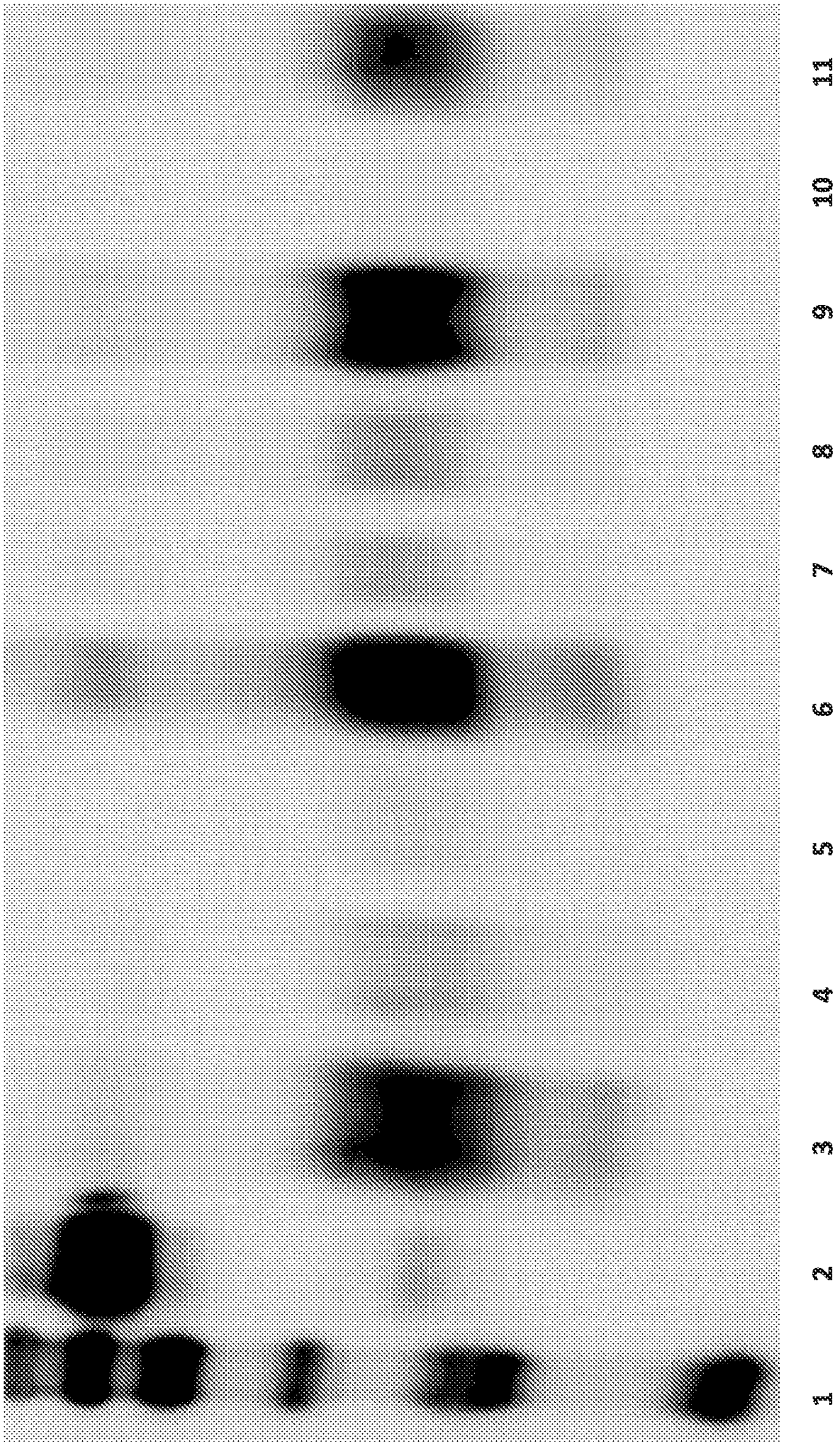
FIG. 2 shows CD63 Western blot analysis of the purification exosomes described in example 6. A description of each lane (from left to right) is as follows: (1) molecular weight markers, (2) CD63-Fc fusion protein, (3) exosome standard, 4E10 particles, (4) exosome standard, 8E9 particles, (5) exosome standard, 3E9 particles, (6) crude clarified feed stream, (7) crude clarified feed stream, 10-fold dilution, (8) column flow through, (9) elution fraction at peak apex, (10) strip, and (11) elution pool (entire peak).
Figure 3:
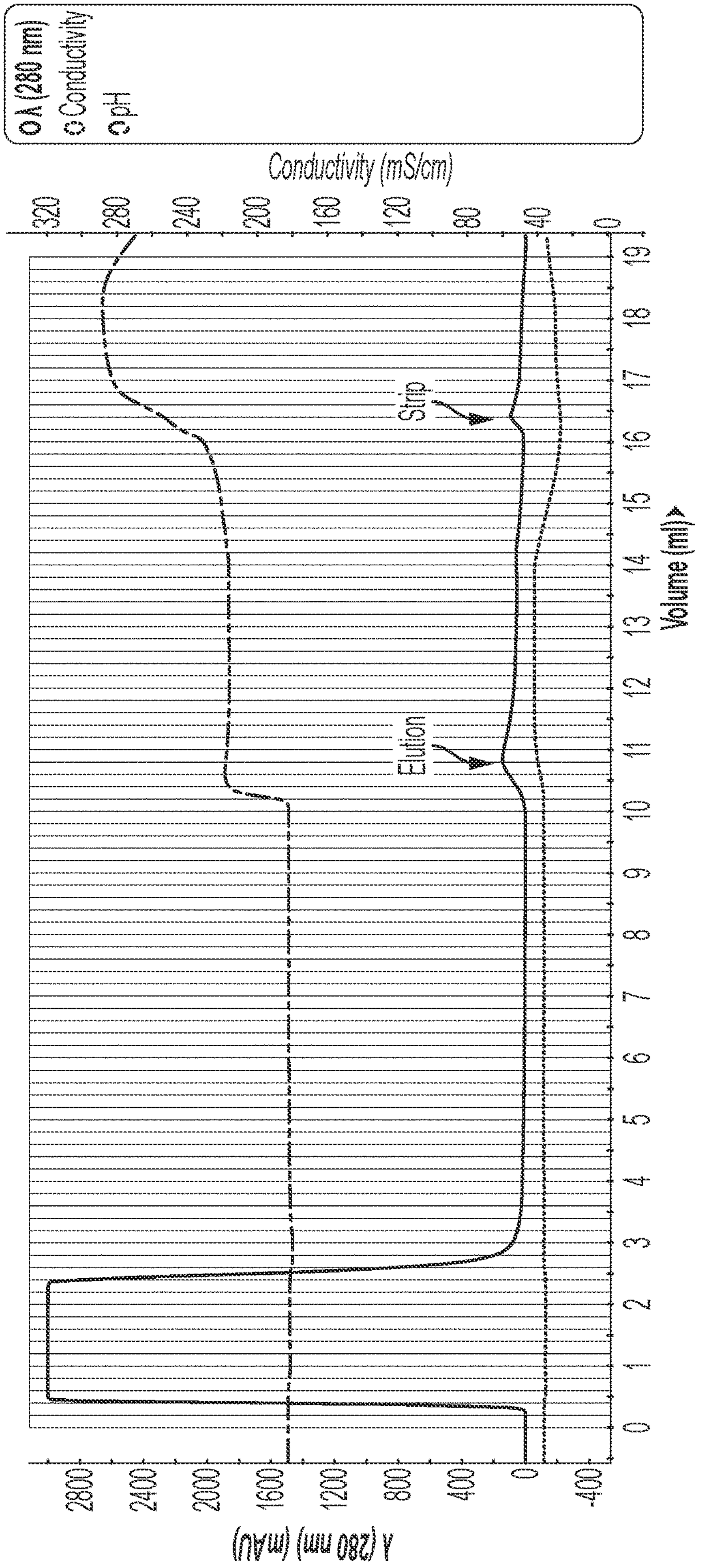
FIG. 3 shows a chromatogram of the purification exosomes described in example 6.

Fractions from the column operation were analyzed by western blotting for the exosome marker CD63, as shown in FIG. 2 and the chromatogram is shown in FIG. 3. The western blot clearly shows that the resin was effective in capturing and eluting exosomes.

Example 7

Figure 4:
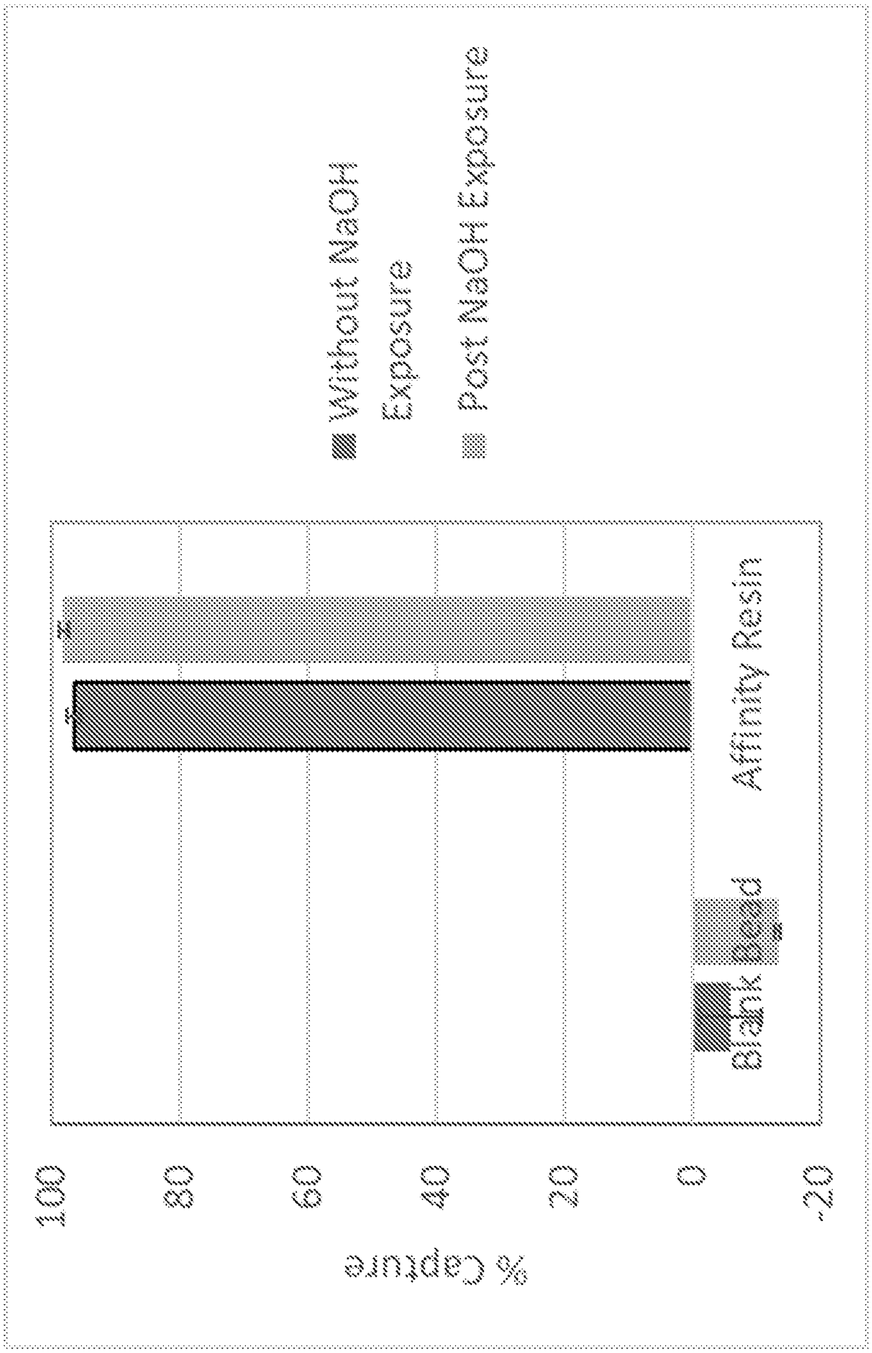
FIG. 4 shows a comparison of the static binding of the resin comprising SEQ ID NO: 43 before and after treatment with 0.1 M NaOH for 18 hours. Blank (Underivatized) beads were included as a control.

This example demonstrates that stability of the affinity agents comprising ligands described herein towards sodium hydroxide. Resin comprising SEQ ID No: 43 was incubated with 0.1 M NaOH for 18 hours, washed and a static binding experiment was conducted as described in example 5. Resin that had not been was incubated with 0.1 M NaOH was included as a control and the comparison of binding is shown in FIG. 4, clearly showing that the resin was stable towards 0.1 M NaOH.

It is contemplated that various combinations or sub-combinations of the specific features and aspects of the embodiments disclosed above may be made and still fall within the invention. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another. Thus, it is intended that the scope of the invention described herein should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described.

Any methods disclosed herein need not be performed in the order recited. The methods disclosed herein include certain actions taken by a practitioner; however, they can also include any third-party instruction of those actions, either expressly or by implication.

TABLE 5

| | SEQUENCES |
|---|---|
| 1 | $X^1$YWRBVWFPHAQGBV$X^2X^2$ |
| 2 | HYWRCVWFPHAQGCVSTA |
| 3 | NYWRCVWFPHAQGCVSTA |
| 4 | SucYWRCVWFPHAQGCVSTA |
| 5 | YWRCVWFPHAQGCVSTA |
| 6 | 3WRCVWFPHAQGCVSTA |
| 7 | Ac-HYWRCVWFPHAQGCVSTA-Amide |
| 8 | Ac-NYWRCVWFPHAQGCVSTA-Amide |
| 9 | SucYWRCVWFPHAQGCVSTA-Amide |
| 10 | Ac-YWRCVWFPHAQGCVSTA-Amide |
| 11 | 3WRCVWFPHAQGCVSTA-Amide |
| 12 | Ac-HYWRCVWFPHAQGCVSTA-(Peg)3K-Amide |
| 13 | Ac-NYWRCVWFPHAQGCVSTA-(Peg)3K-Amide |
| 14 | SucYWRCVWFPHAQGCVSTA-(Peg)3K-Amide |
| 15 | Ac-YWRCVWFPHAQGCVSTA-(Peg)3K-Amide |
| 16 | 3WRCVWFPHAQGCVSTA-(Peg)3K-Amide |
| 17 | HYWR5VWFPHAQG4VSTA |
| 18 | NYWR5VWFPHAQG4VSTA |
| 19 | SucYWR5VWFPHAQG4VSTA |
| 20 | YWR5VWFPHAQG4VSTA |
| 21 | 3WR5VWFPHAQG4VSTA |
| 22 | Ac-HYWR5VWFPHAQG4VSTA-Amide |

TABLE 5-continued

| | SEQUENCES |
|---|---|
| 23 | Ac-NYWR5VWFPHAQG4VSTA-Amide |
| 24 | SucYWR5VWFPHAQG4VSTA-Amide |
| 25 | Ac-YWR5VWFPHAQG4VSTA-Amide |
| 26 | 3WR5VWFPHAQG4VSTA-Amide |
| 27 | Ac-HYWR5VWFPHAQG4VSTA-(Peg)3K-Amide |
| 28 | Ac-NYWR5VWFPHAQG4VSTA-(Peg)3K-Amide |
| 29 | SucYWR5VWFPHAQG4VSTA-(Peg)3K-Amide |
| 30 | Ac-YWR5VWFPHAQG4VSTA-(Peg)3K-Amide |
| 31 | 3WR5VWFPHAQG4VSTA-(Peg)3K-Amide |
| 32 | HYWR5VWFPHAQG2VSTA |
| 33 | NYWR5VWFPHAQG2VSTA |
| 34 | SucYWR5VWFPHAQG2VSTA |
| 35 | YWR5VWFPHAQG2VSTA |
| 36 | 3WR5VWFPHAQG2VSTA |
| 37 | Ac-HYWR5VWFPHAQG2VSTA-Amide |
| 38 | Ac-NYWR5VWFPHAQG2VSTA-Amide |
| 39 | SucYWR5VWFPHAQG2VSTA-Amide |
| 40 | Ac-YWR5VWFPHAQG2VSTA-Amide |
| 41 | 3WR5VWFPHAQG2VSTA-Amide |
| 42 | Ac-HYWR5VWFPHAQG2VSTA-(Peg)3K-Amide |
| 43 | Ac-NYWR5VWFPHAQG2VSTA-(Peg)3K-Amide |
| 44 | SucYWR5VWFPHAQG2VSTA-(Peg)3K-Amide |
| 45 | Ac-YWR5VWFPHAQG2VSTA-(Peg)3K-Amide |
| 46 | 3WR5VWFPHAQG2VSTA-(Peg)3K-Amide |
| 47 | Ac-HYWRCVWFPHAQGCVSTA-(Peg)3K(Biotin)-Amide |
| 48 | Ac-NYWRCVWFPHAQGCVSTA-(Peg)3K(Biotin)-Amide |
| 49 | SucYWRCVWFPHAQGCVSTA-(Peg)3K(Biotin)-Amide |
| 50 | Ac-YWRCVWFPHAQGCVSTA-(Peg)3K(Biotin)-Amide |
| 51 | 3WRCVWFPHAQGCVSTA-(Peg)3K(Biotin)-Amide |
| 52 | Ac-HYWR5VWFPHAQG4VSTA-(Peg)3K(Biotin)-Amide |
| 53 | Ac-NYWR5VWFPHAQG4VSTA-(Peg)3K(Biotin)-Amide |
| 54 | SucYWR5VWFPHAQG4VSTA-(Peg)3K(Biotin)-Amide |
| 55 | Ac-YWR5VWFPHAQG4VSTA-(Peg)3K(Biotin)-Amide |
| 56 | 3WR5VWFPHAQG4VSTA-(Peg)3K(Biotin)-Amide |
| 57 | Ac-HYWR5VWFPHAQG2VSTA-(Peg)3K(Biotin)-Amide |
| 58 | Ac-NYWR5VWFPHAQG2VSTA-(Peg)3K(Biotin)-Amide |
| 59 | SucYWR5VWFPHAQG2VSTA-(Peg)3K(Biotin)-Amide |
| 60 | Ac-YWR5VWFPHAQG2VSTA-(Peg)3K(Biotin)-Amide |
| 61 | 3WR5VWFPHAQG2VSTA-(Peg)3K(Biotin)-Amide |
| 62 | Ac-HYWRCVWFPHAQGCVATA-(Peg)3K(Biotin)-Amide |
| 63 | Ac-NYWRCVWFPHAQGCVATA-(Peg)3K(Biotin)-Amide |
| 64 | SucYWRCVWFPHAQGCVATA-(Peg)3K(Biotin)-Amide |
| 65 | Ac-YWRCVWFPHAQGCVATA-(Peg)3K(Biotin)-Amide |
| 66 | 3WRCVWFPHAQGCVATA-(Peg)3K(Biotin)-Amide |
| 67 | Ac-HYWR5VWFPHAQG4VATA-(Peg)3K(Biotin)-Amide |
| 68 | Ac-NYWR5VWFPHAQG4VATA-(Peg)3K(Biotin)-Amide |
| 69 | SucYWR5VWFPHAQG4VATA-(Peg)3K(Biotin)-Amide |
| 70 | Ac-YWR5VWFPHAQG4VATA-(Peg)3K(Biotin)-Amide |
| 71 | 3WR5VWFPHAQG4VATA-(Peg)3K(Biotin)-Amide |
| 72 | Ac-HYWR5VWFPHAQG2VATA-(Peg)3K(Biotin)-Amide |
| 73 | Ac-NYWR5VWFPHAQG2VATA-(Peg)3K(Biotin)-Amide |
| 74 | SucYWR5VWFPHAQG2VATA-(Peg)3K(Biotin)-Amide |
| 75 | Ac-YWR5VWFPHAQG2VATA-(Peg)3K(Biotin)-Amide |
| 76 | 3WR5VWFPHAQG2VATA-(Peg)3K(Biotin)-Amide |
| 77 | Ac-HYWRCVWFPHAQGCVSTAPEGGK(Biotin)-Amide |
| 78 | Ac-NYWRCVWFPHAQGCVSTAPEGGK(Biotin)-Amide |
| 79 | SucYWRCVWFPHAQGCVSTAPEGGK(Biotin)-Amide |
| 80 | Ac-YWRCVWFPHAQGCVSTAPEGGK(Biotin)-Amide |
| 81 | 3WRCVWFPHAQGCVSTAPEGGK(Biotin)-Amide |
| 82 | Ac-HYWR5VWFPHAQG4VSTAPEGGK(Biotin)-Amide |
| 83 | Ac-NYWR5VWFPHAQG4VSTAPEGGK(Biotin)-Amide |
| 84 | SucYWR5VWFPHAQG4VSTAPEGGK(Biotin)-Amide |
| 85 | Ac-YWR5VWFPHAQG4VSTAPEGGK(Biotin)-Amide |
| 86 | 3WR5VWFPHAQG4VSTAPEGGK(Biotin)-Amide |
| 87 | Ac-HYWR5VWFPHAQG2VSTAPEGGK(Biotin)-Amide |
| 88 | Ac-NYWR5VWFPHAQG2VSTAPEGGK(Biotin)-Amide |
| 89 | SucYWR5VWFPHAQG2VSTAPEGGK(Biotin)-Amide |
| 90 | Ac-YWR5VWFPHAQG2VSTAPEGGK(Biotin)-Amide |
| 91 | 3WR5VWFPHAQG2VSTAPEGGK(Biotin)-Amide |
| 92 | Ac-HYWRCVWFPHAQGCVATAPEGGK(Biotin)-Amide |
| 93 | Ac-NYWRCVWFPHAQGCVATAPEGGK(Biotin)-Amide |
| 94 | SucYWRCVWFPHAQGCVATAPEGGK(Biotin)-Amide |
| 95 | Ac-YWRCVWFPHAQGCVATAPEGGK(Biotin)-Amide |
| 96 | 3WRCVWFPHAQGCVATAPEGGK(Biotin)-Amide |
| 97 | Ac-HYWR5VWFPHAQG4VATAPEGGK(Biotin)-Amide |
| 98 | Ac-NYWR5VWFPHAQG4VATAPEGGK(Biotin)-Amide |
| 99 | SucYWR5VWFPHAQG4VATAPEGGK(Biotin)-Amide |
| 100 | Ac-YWR5VWFPHAQG4VATAPEGGK(Biotin)-Amide |

TABLE 5-continued

| | SEQUENCES |
|---|---|
| 101 | 3WR5VWFPHAQG4VATAPEGGK(Biotin)-Amide |
| 102 | Ac-HYWR5VWFPHAQG2VATAPEGGK(Biotin)-Amide |
| 103 | Ac-NYWR5VWFPHAQG2VATAPEGGK(Biotin)-Amide |
| 104 | SucYWR5VWFPHAQG2VATAPEGGK(Biotin)-Amide |
| 105 | Ac-YWR5VWFPHAQG2VATAPEGGK(Biotin)-Amide |
| 106 | 3WR5VWFPHAQG2VATAPEGGK(Biotin)-Amide |
| 107 | HYWR5VWFPHAQG2VATA |
| 108 | NYWR5VWFPHAQG2VATA |
| 109 | SucYWR5VWFPHAQG2VATA |
| 110 | YWR5VWFPHAQG2VATA |
| 111 | 3WR5VWFPHAQG2VATA |
| 112 | Ac-HYWR5VWFPHAQG2VATA-Amide |
| 113 | Ac-NYWR5VWFPHAQG2VATA-Amide |
| 114 | SucYWR5VWFPHAQG2VATA-Amide |
| 115 | Ac-YWR5VWFPHAQG2VATA-Amide |
| 116 | 3WR5VWFPHAQG2VATA-Amide |
| 117 | Ac-HYWR5VWFPHAQG2VATA-(Peg)3K-Amide |
| 118 | Ac-NYWR5VWFPHAQG2VATA-(Peg)3K-Amide |
| 119 | SucYWR5VWFPHAQG2VATA-(Peg)3K-Amide |
| 120 | Ac-YWR5VWFPHAQG2VATA-(Peg)3K-Amide |
| 121 | 3WR5VWFPHAQG2VATA-(Peg)3K-Amide |
| 122 | Ac-HYWR5VWFPHAQG2VATAPEGGK-Amide |
| 123 | Ac-NYWR5VWFPHAQG2VATAPEGGK-Amide |
| 124 | SucYWR5VWFPHAQG2VATAPEGGK-Amide |
| 125 | Ac-YWR5VWFPHAQG2VATAPEGGK-Amide |
| 126 | 3WR5VWFPHAQG2VATAPEGGK-Amide |

$X^1$=H or N
$X^2$-=S or T
Ac- denotes N-terminal acetylation
-Amide denotes C-terminal amidation
5 denotes an aspartic acid residue in which the carboxyl sidechain is conjugated to either an épsilon amino group of a lysine residue that is denoted by 4, or the beta amino group of a 2,3-diaminopropionic acid residue that is denoted by a 2.
Suc denotes succinate (butanedioic acid)
3 denotes 3-(4-hydroxyphenyl)propionate
(Peg)3- denotes 12-amino-4,7,10-trioxadodecanoic acid subunits
Cysteine residues may form intramolecular disulfide bonds

The invention claimed is:

1. An affinity agent comprising a ligand that binds to cluster of differentiation 81 ("CD81"), wherein the ligand comprises the cyclic peptide comprising the amino acid sequence $X^1YWRB^1VWFPHAQGB^2VX^2 X^3$, SEQ ID NO: 1 wherein $X^1$ is H or N or is deleted, $X^2$ is A or S, $X^3$ is T and $B^1$ and $B^2$ are independently any amino acid through which the peptide is cyclized, optionally wherein the amino acid sequence of the cyclic peptide comprises an N- or C-terminal modification selected from glycosylation, acetylation, benzylation, phosphorylation, amidation, pegylation, or formylation.

2. The affinity agent of claim 1, wherein $B^1$ of the cyclic peptide is aspartic acid and $B^2$ is either lysine or 2,3-diaminopropionic acid.

3. The affinity agent of claim 1, wherein the cyclic peptide is acetylated at the N-terminus and/or amidated at the C-terminus.

4. The affinity agent of claim 1, wherein a linker peptide is attached to the C-terminus of SEQ ID NO: 1, and wherein the linker peptide is 1 to 10 amino acids in length.

5. The affinity agent of claim 4, wherein the linker peptide comprises a reactive residue selected from lysine or cysteine.

6. The affinity agent of claim 1, wherein the cyclic peptide comprises the amino acid sequence selected from SEQ ID NOs: 77, 78, 82, 83, 87, and 88.

7. The affinity agent of claim 1, wherein a C-terminal non-peptide linker is attached to the C-terminus of the cyclic peptide.

8. The affinity agent of claim 7, wherein the C-terminal non-peptide linker is an alkyl linker or a polyethylene glycol (PEG) linker.

9. The affinity agent of claim 8, wherein the C-terminal non-peptide linker is an alkyl linker and the alkyl linker comprises 12-amino-4,7,10-trioxadodecanoic acid.

10. The affinity agent of claim 1, wherein the cyclic peptide comprises the amino acid sequence selected from SEQ ID NOs: 2, 3, 7, 8, 12, 13, 17, 18, 22, 23, 27, 28, 32, 33, 37, 38, 42, 43, 47, 48, 52, 53, 57, and 58.

11. The affinity agent of claim 1, wherein the ligand is attached to a solid surface.

12. The affinity agent of claim 11, wherein the solid surface is a resin, a bead, a membrane, or a monolith.

13. The affinity agent of claim 1, wherein the cyclic peptide comprises the amino acid sequence selected from SEQ ID NOs: 17, 22, 27, 32, 37, 42, 52, 57, 82 and 87.

14. An affinity agent comprising a ligand that binds to CD81, said ligand comprising a cyclic peptide comprising the amino acid sequence selected from SEQ ID NOs: 4-6, 9-11, 14-16, 19-21, 24-26, 29-31, 34-36, 39-41, 44-46, 49-51, 54-56, 59-61, 79-81, 84-86, and 89-91.

15. An affinity agent comprising a ligand that binds to CD81, said ligand comprising a cyclic peptide comprising the amino acid sequence selected from SEQ ID NOs: 62-76 and 107-121.

16. An affinity agent comprising a ligand that binds to CD81, said ligand comprising a cyclic peptide comprising the amino acid sequence selected from SEQ ID NOs: 92-106 and 122.

17. An affinity agent comprising a ligand that binds to CD81, said ligand comprising a cyclic peptide comprising the amino acid sequence selected from SEQ ID NOs: 17, 22, 27, 32, 37, 42, 52, 57, 82 and 87.

18. A method for purification of one or more exosomes, the method comprising contacting the affinity agent of claim 11 with a solution comprising the exosomes.

19. A method for purification of one or more exosomes, the method comprising contacting the affinity agent of claim 13 with a solution comprising the exosomes, optionally wherein the ligand is attached to a solid surface.

20. The method of claim 19, wherein the solid surface is a resin, a bead, a membrane, or a monolith.

* * * * *